United States Patent [19]
Kuberasampath et al.

[11] Patent Number: 6,090,776
[45] Date of Patent: *Jul. 18, 2000

[54] MORPHOGEN TREATMENT OF ORGAN IMPLANTS

[75] Inventors: Thangavel Kuberasampath, Medway, Mass.; Roy H. L. Pang, Etna, N.H.; Hermann Oppermann, Medway, Mass.; David C. Rueger, Hopkinton, Mass.; Charles M. Cohen, Medway, Mass.; John E. Smart, Weston, Mass.

[73] Assignee: Creative Bio Molecules, Inc., Boston, Mass.

[ * ] Notice: This patent is subject to a terminal disclaimer.

[21] Appl. No.: 08/480,515

[22] Filed: Jun. 7, 1995

Related U.S. Application Data

[63] Continuation of application No. 08/152,901, Nov. 15, 1993, abandoned, which is a continuation of application No. 07/938,337, Aug. 28, 1992, abandoned, which is a continuation-in-part of application No. 07/753,059, Aug. 30, 1991, abandoned, which is a continuation-in-part of application No. 07/667,274, Mar. 11, 1991, abandoned, which is a continuation-in-part of application No. 07/752,764, Aug. 30, 1991, abandoned, which is a continuation-in-part of application No. 07/667,274, Mar. 11, 1991, abandoned, and a continuation-in-part of application No. 07/938,336, Aug. 28, 1992, abandoned.

[51] Int. Cl.$^7$ .......................... A61K 38/16; A61K 38/17; A61K 38/18
[52] U.S. Cl. ...................... 514/2; 514/8; 514/12
[58] Field of Search .................. 514/2, 8, 12; 435/69.1; 530/350, 399

[56] References Cited

U.S. PATENT DOCUMENTS

| | | |
|---|---|---|
| 4,388,309 | 6/1983 | Fibricius et al. .......................... 514/12 |
| 4,450,159 | 5/1984 | Anderson et al. ................... 514/227.2 |
| 4,473,637 | 9/1984 | Guibert ........................................ 435/1 |
| 4,877,864 | 10/1989 | Wang et al. .............................. 514/12 |
| 4,968,590 | 11/1990 | Kuberasampath et al. ............. 530/326 |
| 4,971,952 | 11/1990 | Bentz et al. ............................... 514/12 |
| 4,975,526 | 12/1990 | Kuberasampath et al. ............. 530/350 |
| 5,002,965 | 3/1991 | Ramwell et al. ....................... 424/423 |
| 5,011,691 | 4/1991 | Oppermann et al. .................. 435/69.1 |
| 5,013,649 | 5/1991 | Wang et al. .......................... 530/387.3 |
| 5,091,513 | 2/1992 | Huston et al. ........................ 530/387.3 |
| 5,106,626 | 4/1992 | Parsons et al. ......................... 424/423 |
| 5,108,753 | 4/1992 | Kuberasampath et al. ............. 424/422 |
| 5,118,791 | 6/1992 | Burnier et al. . |
| 5,135,915 | 8/1992 | Czarniecki et al. . |
| 5,141,905 | 8/1992 | Rosen et al. .......................... 435/69.1 |

FOREIGN PATENT DOCUMENTS

| | | |
|---|---|---|
| 0148155 | 1/1985 | European Pat. Off. . |
| 0 269 408 | 6/1988 | European Pat. Off. ....... A61K 37/02 |
| 0416578 | 9/1990 | European Pat. Off. . |
| WO84/01106 | 3/1984 | WIPO . |
| 88/00205 | 1/1988 | WIPO . |
| 89/09787 | 10/1989 | WIPO . |
| 89/09788 | 10/1989 | WIPO . |
| 89/10409 | 11/1989 | WIPO . |
| 90/00900 | 2/1990 | WIPO ............................ A61K 37/36 |
| 90/03733 | 4/1990 | WIPO . |
| 91/05802 | 5/1991 | WIPO ............................ C07K 15/00 |
| 92/07073 | 4/1992 | WIPO ............................ C07K 15/00 |
| 92/15323 | 9/1992 | WIPO ............................ A61K 37/12 |

OTHER PUBLICATIONS

Noda et al. Endocrinology 124:2991–2994, 1989.
Joyce et al. Annals of the New York Academy of Sciences 593:107–123, 1990.
Beck et al. J. Bone Min. Res. 6:1257–1265, 1991.
Puolakkainen et al. J. Surg. Res. 58:321–329, 1995.
Alberts et al., Molecular Biology of the Cell, 3rd edition, Garland Publishing Inc., New York, p. 937, 1994.
Sampath et al. (1983), "Homology of Bone–Inductive Proteins From Human, Monkey, Bovine and Rat Extracellular Matrix," 80 *Proc. Nat'l Acad. Sci. USA* 6591–6595.
Bentz et al. (1987), "Cartilage Induction and Differentiation: The Role of Bone Derived Cartilage Inducing Factor (CIF–A)," *Dev. & Diseases of Cartil. & Bone Matrix* 137–147.
Ruscetti et al. (1991), "Transforming Growth Factor–β And The Immune System," 3 *Prog. Growth Factor Res.* 159–175.
Sporn et al. (1992), "Transforming Growth Factor–β: Recent Progress and New Challenges," 119 *J. Cell Biol.* 1017–1021.
Gross et al. (1993), "Transforming Growth Factor–β1 Reduces Infarct Size After Experimental Cerebral Ischemia in a Rabbit Model," 24 *Stroke* 558–562.
Reddi et al. (1993), "Initiation and Promotion of Bone Differentiation by Bone Morphogenetic Proteins," 8 *J. Bone. Min. Res.* 2:S499–S502.
Sampath et al. (1994), "Structure, Function, and Orthopedic Applications of Osteogenic Protein–1 (OP–1)," *Complications in Orthop.* 101–107.
Behringer et al., *Nature*, 345:167–170 (1990).
Cate et al., *Cell*, 45:685–698 (1986).
Celeste et al., *PNAS*, 87:9843–9847 (1991).
Chomczyaski et al., *Anal. Biochem*, 162:156–159 (1987).
Green et al., *Nature*, 347:391–394 (1990).
Kuberasampath et al., *J. Biol. Chem.*, 265:13198–13205 (1990).
Lee, *Molecular Endocrinology*, 90:1034–1040 (1990).
Lee, *PNAS*, 88:4250–4254 (1991).
Lyons et al., *PNAS*, 86:4554–4558 (1989).

(List continued on next page.)

*Primary Examiner*—Elizabeth Kemmerer
*Attorney, Agent, or Firm*—Mintz, Levin, Cohn, Ferris, Glovisky and Popeo, P.C.; Ivor R. Elaifi; Michael Morency

[57] ABSTRACT

The present invention is directed to methods and compositions for enhancing viability of organs and living tissues to be transplanted in a mammal. The methods and compositions provide a therapeutically effective concentration of a morphogen or morphogen-stimulating agent to the tissue or organ to be transplanted, sufficient to substantially protect the tissue or organ from tissue damage.

6 Claims, 5 Drawing Sheets

OTHER PUBLICATIONS

Lyons et al., *Genes & Development,* 3:1657–1668 (1989).
Mason et al., *Nature,* 318:659–663 (1985).
Mason et al., *Mol. Endocrinology,* 3:1352–1358 (1989).
Miller et al., *Cancer Research,* 42:2589–3594 (1987).
Ozkaynak et al., *Embo J.,* 9:2085–2093 (1990).
Ozkaynak et al., *Biochem. Biophys. Res. Comm.,* 179:116–123 (1991).
Padgett et al., *Nature,* 325:81–84 (1987).
Panganiban et al., *Mol. and Cell. Biol.,* 10:2669–2677 (1990).
Sampath et al., *PNAS,* 80:6591–6595 (1983).
Schubert et al., *Nature,* 344:868–870 (1990).
Smith et al., *Nature,* 345:729–731 (1990).
Sokol et al., *Science,* 249:561–563 (1990).
Wang et al., *PNAS,* 87:2220–2224 (1990).
Wang et al., *PNAS,* 85:9484–9488 (1988).
Weeks, *Cell,* 51:861–867 (1987).
Wharton et al., *PNAS,* 88:9214–9218 (1991).
Wozney et al., *Science,* 242:1528–1534 (1988).
Yannas, *Angew. Chem. Int. Ed. Engl.,* 29:20–35 (1990).
Rosen et al., Wang et al., and Wozney et al., "Development Expression of Cartilage and E–Specific Genes in the Rat Embryo", "Identification Through Molecular Cloning of Factors Involved in In Vivo Cartilage Formation", *Calcified Tissue Int,* 42 (Suppl.): A35(136), A37(146,147) 3 Abstracts (1988).
Rosen et al., "Purification and Molecular Cloning of a Novel Group of BMPS and Localization of BMP MRNA in Developing Bone", *Connect Tissue Res,* 20(1–4): 313–9.
Wozney et al., "Bone Morphogenetic Proteins", *Progress In Growth Factor Research,* 1: 267–280 (1990).
2 Abstracts, Rosen et al., "In Vivo and In Vitro Roles of BMP in Skeletal Formation and Repair", and Celeste et al., "Highly Purified Bovine Bone–Inductive Activity Contains Multiple Protein Species Related to BMP–2", *J Cell Biochem Suppl.* 0 (14 Part E): 33(004), 54(105) (1990).
Katagiri et al., "The Non–Osteogenenic Mouse Pluripotent Cell Line, C3H10T1/2, is Induced to Differentiate Into Osteoblastic Cells by Recombinant Human Bone Morphogenetic Protein–2", *Biochem. Biophys Res,* (172, (1): 295–299 (1990).
Wozney et al., "Growth factors influencing bone development", *Journal of Cell Science Suppl.,* 13: 149–156 (1990).
Celeste et al., "Identification of transforming growth factor β family members present in bone–inductive protein purified from bovine bone", *PNAS,* 87: 9843–9847 (1990).
Takuwa et al., "Bone Morphogenetic Protein–2 Stimulates Alkaline Phosphatase Activity and Collagen Synthesis in Cultured Osteoblastic Cells, MC3T3–E1", *Biochem Biophys Res Comm,* 174(1):96–101 (1991).

Yamaguchi et al., "Recombinant Human Bone Morphogenetic Protein–2 Stimulates Osteoblastic Maturation and Inhibits Myogenic Differentiation In Vitro", *J Cell Biol,* 113 (3): 681–7 (1991).

Abstract Q–105 D'Alessandro et al., "Purification Characterization and Activity of Recombinant Human BMP–5", *Journal of Cellular Biochemistry,* (1991).

Abstract Q–111, Israel et al., "Expression of Recombinant BMP2 in Chinese Hamster Ovary Cells", *Journal of Cellular Biochemistry,* (1991).

Thies et al., "Recombinant Human Bone Morphogenetic Protein–2 Induces Osteoblastic Differentiation in W–20–17 Stromal Cells", *Endocrinology,* 130(3):1318–1324 (1992).

Wozney et al., "The Bone Morphogenetic Protein Family and Osteogenesis", *Mol Reprod Dev,* 32 (2): 160–167 (1992).

Rogers et al., "Bone Morphogenetic Proteins–2 and –4 are Involved in the Retinoic Acid–Induced Differentiation of Embryonal Carcinoma Cells", *Mol Biol Cell,* 3 (2): 289–196 (1992).

3 Abstracts, Rosen et al., "Isolation and Characterization of BMP–Responsive Cartilage and Bone Cell Progenitors From Mouse Embryo Limb Buds", Celeste et al., "Molecular Cloning of BMP–8: A Protein Present in Bovine Bone Which is Highly Related to the BMP–5/6/7 Subfamily of Osteoinductive Molecules", and Wozney et al., "Regulation of Chondrogenesis and Osteogenesis by the BMP Proteins", *J Cell Biochem Suppl,* 0 (16 Part F): 103(W513); 100(W502): 76(W026) (1992).

Israel et al., "Expression and Characterization of Bone Morphogenetic Protein–2 in Chinese Hamster Ovary Cells", *Growth Factors,* 7: 139–150 (1992).

Padgett et al., "Human BMP sequences can confer normal dorsal–ventral patterning in the Drosophila embyro", *Proce. Natl. Acad. Sci. USA,* 90: 2905–2909 (1993).

Bowie et al. 1990. Science 247: 1306–1310.

Ngo et al. 1994. *The Protein Folding Problem and Tertiary Structure Prediction,* Merz et al., eds., pp. 491–495., Birkhauser Press, Boston.

George et al. (1988) Macromolecular Sequencing and Synthesis (Alan R. Liss, Inc., N.Y) pp. 127–149.

Gennaro (1990) Remington's Pharmaceutical Sciences (Mack Pubs., N.Y.).

Lefer et al. (1990) Science 249: 61–64.

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 97 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..97
      (D) OTHER INFORMATION: /label= GENERIC-SEQ-1
          /note= "EACH XAA INDICATES ONE OF THE 20 NATURALLY
          OCCURRING L-ISOMER, ALPHA-AMINO ACIDS, OR A DERIVATIVE
          THEREOF"

(xi) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Cys Xaa Xaa Xaa Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
            85                  90                  95

Xaa
```

(2) INFORMATION FOR SEQ ID NO:2:

(i) SEQUENCE CHARACTERISTICS:
      (A) LENGTH: 97 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..97
      (D) OTHER INFORMATION: /label= GENERIC-SEQ-2
          /note= "EACH XAA INDICATES ONE OF THE 20 NATURALLY

OCCURING L-ISOMER, ALPHA-AMINO ACIDS, OR A DERIVATIVE
THEREOF"

(xi) SEQUENCE DESCRIPTION: SEQ ID NO:2:

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Cys Xaa Xaa Xaa Cys Xaa Xaa Xaa
            20                  25                  30

Xaa Xaa Xaa Cys Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Cys Cys Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Cys
            85                  90                  95

Xaa
```

(2) INFORMATION FOR SEQ ID NO:3:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= GENERIC-SEQ-3
            /note= "WHEREIN EACH XAA IS INDEPENDENTLY SELECTED FROM A
            GROUP OF ONE OR MORE SPECIFIED AMINO ACIDS AS DEFINED IN
            THE SPECIFICATION "

(xi) SEQUENCE DESCRIPTION: SEQ ID NO:3:

```
Leu Tyr Val Xaa Phe Xaa Xaa Xaa Gly Trp Xaa Xaa Trp Xaa Xaa Ala
 1               5                  10                  15

Pro Xaa Gly Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Leu
            35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Gly Cys
            85                  90                  95

Xaa
```

(2) INFORMATION FOR SEQ ID NO:4:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein (B) LOCATION: 1..102
            (D) OTHER INFORMATION: /label= GENERIC-SEQ-4
                /note= "WHEREIN EACH XAA IS INDEPENDENTLY SELECTED FROM A
                GROUP OF ONE OR MORE SPECIFIED AMINO ACIDS AS DEFINED IN
                THE SPECIFICATION"

(xi) SEQUENCE DESCRIPTION: SEQ ID NO:4:

Cys Xaa Xaa Xaa Xaa Leu Tyr Val Xaa Phe Xaa Xaa Xaa Gly Trp Xaa
1               5                   10                  15

Xaa Trp Xaa Xaa Ala Pro Xaa Gly Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Leu Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Gly Cys Xaa
            100

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "HOP-1 (MATURE FORM)"

(xi) SEQUENCE DESCRIPTION: SEQ ID NO:5:

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
            130                 135

(2) INFORMATION FOR SEQ ID NO:6:

(i) SEQUENCE CHARACTERISTICS:
        (A) LENGTH: 139 amino acids (B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..139
(D) OTHER INFORMATION: /note= "MOP-1 (MATURE FORM)"

(xi) SEQUENCE DESCRIPTION: SEQ ID NO:6:

```
Ser Thr Gly Gly Lys Gln Arg Ser Gln Asn Arg Ser Lys Thr Pro Lys
  1               5                  10                  15

Asn Gln Glu Ala Leu Arg Met Ala Ser Val Ala Glu Asn Ser Ser Ser
             20                  25                  30

Asp Gln Arg Gln Ala Cys Lys Lys His Glu Leu Tyr Val Ser Phe Arg
             35                  40                  45

Asp Leu Gly Trp Gln Asp Trp Ile Ile Ala Pro Glu Gly Tyr Ala Ala
 50                  55                  60

Tyr Tyr Cys Glu Gly Glu Cys Ala Phe Pro Leu Asn Ser Tyr Met Asn
 65                  70                  75                  80

Ala Thr Asn His Ala Ile Val Gln Thr Leu Val His Phe Ile Asn Pro
             85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
            115                 120                 125

Arg Asn Met Val Val Arg Ala Cys Gly Cys His
            130                 135
```

(2) INFORMATION FOR SEQ ID NO:7:

(i) SEQUENCE CHARACTERISTICS:
(A) LENGTH: 139 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..139
(D) OTHER INFORMATION: /note= "HOP-2 (MATURE FORM)"

(xi) SEQUENCE DESCRIPTION: SEQ ID NO:7:

```
Ala Val Arg Pro Leu Arg Arg Arg Gln Pro Lys Lys Ser Asn Glu Leu
  1               5                  10                  15

Pro Gln Ala Asn Arg Leu Pro Gly Ile Phe Asp Asp Val His Gly Ser
             20                  25                  30

His Gly Arg Gln Val Cys Arg Arg His Glu Leu Tyr Val Ser Phe Gln
             35                  40                  45

Asp Leu Gly Trp Leu Asp Trp Val Ile Ala Pro Gln Gly Tyr Ser Ala
 50                  55                  60

Tyr Tyr Cys Glu Gly Glu Cys Ser Phe Pro Leu Asp Ser Cys Met Asn
 65                  70                  75                  80

Ala Thr Asn His Ala Ile Leu Gln Ser Leu Val His Leu Met Lys Pro
             85                  90                  95

Asn Ala Val Pro Lys Ala Cys Cys Ala Pro Thr Lys Leu Ser Ala Thr
            100                 105                 110
```

```
Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135
```

(2) INFORMATION FOR SEQ ID NO:8:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..139
        (D) OTHER INFORMATION: /note= "MOP-2 (MATURE FORM)"

(xi) SEQUENCE DESCRIPTION: SEQ ID NO:8:

```
Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135
```

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2A(FX)"

(xi) SEQUENCE DESCRIPTION: SEQ ID NO:9:

```
Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
```

```
            50                  55                  60
Cys Cys Val Pro Thr Glu Leu Ser Ala Ile Ser Met Leu Tyr Leu Asp
 65                  70                  75                  80

Glu Asn Glu Lys Val Val Leu Lys Asn Tyr Gln Asp Met Val Val Glu
                 85                  90                  95

Gly Cys Gly Cys Arg
            100
```

(2) INFORMATION FOR SEQ ID NO:10:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..101
        (D) OTHER INFORMATION: /note= "CBMP-2B(FX)"

(xi) SEQUENCE DESCRIPTION: SEQ ID NO:10:

```
Cys Arg Arg His Ser Leu Tyr Val Asp Phe Ser Asp Val Gly Trp Asn
 1                   5                  10                  15

Asp Trp Ile Val Ala Pro Pro Gly Tyr Gln Ala Phe Tyr Cys His Gly
                 20                  25                  30

Asp Cys Pro Phe P

```
Ala Cys Cys Val Pro Thr Gln Leu Asp Ser Val Ala Met Leu Tyr Leu
 65                  70                  75                  80

Asn Asp Gln Ser Thr Val Val Leu Lys Asn Tyr Gln Glu Met Thr Val
                 85                  90                  95

Val Gly Cys Gly Cys Arg
            100
```

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGL(FX)"

(xi) SEQUENCE DESCRIPTION: SEQ ID NO:12:

```
Cys Lys Lys Arg His Leu Tyr Val Glu Phe Lys Asp Val Gly Trp Gln
 1               5                  10                  15

Asn Trp Val Ile Ala Pro Gln Gly Tyr Met Ala Asn Tyr Cys Tyr Gly
                 20                  25                  30

Glu Cys Pro Tyr Pro Leu Thr Glu Ile Leu Asn Gly Ser Asn His Ala
                 35                  40                  45

Ile Leu Gln Thr Leu Val His Ser Ile Glu Pro Glu Asp Ile Pro Leu
 50                  55                  60

Pro Cys Cys Val Pro Thr Lys Met Ser Pro Ile Ser Met Leu Phe Tyr
 65                  70                  75                  80

Asp Asn Asn Asp Asn Val Val Leu Arg His Tyr Glu Asn Met Ala Val
                 85                  90                  95

Asp Glu Cys Gly Cys Arg
            100
```

(2) INFORMATION FOR SEQ ID NO:13:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /note= "VGR-1(FX)"

(xi) SEQUENCE DESCRIPTION: SEQ ID NO:13:

```
Cys Lys Lys His Glu Leu Tyr Val Ser Phe Gln Asp Val Gly Trp Gln
 1               5                  10                  15

Asp Trp Ile Ile Ala Pro Lys Gly Tyr Ala Ala Asn Tyr Cys Asp Gly
                 20                  25                  30

Glu Cys Ser Phe Pro Leu Asn Ala His Met Asn Ala Thr Asn His Ala
                 35                  40                  45

Ile Val Gln Thr Leu Val His Val Met Asn Pro Glu Tyr Val Pro Lys
 50                  55                  60
```

```
Pro Cys Cys Ala Pro Thr Lys Val Asn Ala Ile Ser Val Leu Tyr Phe
 65                  70                  75                  80

Asp Asp Asn Ser Asn Val Ile Leu Lys Lys Tyr Arg Asn Met Val Val
                 85                  90                  95

Arg Ala Cys Gly Cys His
            100
```

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..106
        (D) OTHER INFORMATION: /note= "GDF-1 (FX)"

(xi) SEQUENCE DESCRIPTION: SEQ ID NO:14:

```
Cys Arg Ala Arg Arg Leu Tyr Val Ser Phe Arg Glu Val Gly Trp His
 1               5                  10                  15

Arg Trp Val Ile Ala Pro Arg Gly Phe Leu Ala Asn Tyr Cys Gln Gly
                 20                  25                  30

Gln Cys Ala Leu Pro Val Ala Leu Ser Gly Ser Gly Gly Pro Pro Ala
             35                  40                  45

Leu Asn His Ala Val Leu Arg Ala Leu Met His Ala Ala Ala Pro Gly
 50                  55                  60

Ala Ala Asp Leu Pro Cys Cys Val Pro Ala Arg Leu Ser Pro Ile Ser
 65                  70                  75                  80

Val Leu Phe Phe Asp Asn Ser Asp Asn Val Val Leu Arg Gln Tyr Glu
                 85                  90                  95

Asp Met Val Val Asp Glu Cys Gly Cys Arg
                100                 105
```

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Cys Xaa Xaa Xaa Xaa
 1               5
```

(2) INFORMATION FOR SEQ ID NO:16:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 49..1341
        (D) OTHER INFORMATION: /product= "HOP-1"

(xi) SEQUENCE DESCRIPTION: SEQ ID NO:16:

| | | | | | | | |
|---|---|---|---|---|---|---|---|
| GGTGCGGGCC CGGAGCCCGG AGCCCGGGTA GCGCGTAGAG CCGGCGCG ATG CAC GTG | | | | | | | 57 |
| | | | | | Met | His | Val |
| | | | | | 1 | | |

| CGC | TCA | CTG | CGA | GCT | GCG | GCG | CCG | CAC | AGC | TTC | GTG | GCG | CTC | TGG | GCA | 105 |
|---|---|---|---|---|---|---|---|---|---|---|---|---|---|---|---|---|
| Arg | Ser | Leu | Arg | Ala | Ala | Ala | Pro | His | Ser | Phe | Val | Ala | Leu | Trp | Ala | |
| | 5 | | | | 10 | | | | | 15 | | | | | | |

| CCC | CTG | TTC | CTG | CTG | CGC | TCC | GCC | CTG | GCC | GAC | TTC | AGC | CTG | GAC | AAC | 153 |
|---|---|---|---|---|---|---|---|---|---|---|---|---|---|---|---|---|
| Pro | Leu | Phe | Leu | Leu | Arg | Ser | Ala | Leu | Ala | Asp | Phe | Ser | Leu | Asp | Asn | |
| 20 | | | | | 25 | | | | | 30 | | | | | 35 | |

| GAG | GTG | CAC | TCG | AGC | TTC | ATC | CAC | CGG | CGC | CTC | CGC | AGC | CAG | GAG | CGG | 201 |
|---|---|---|---|---|---|---|---|---|---|---|---|---|---|---|---|---|
| Glu | Val | His | Ser | Ser | Phe | Ile | His | Arg | Arg | Leu | Arg | Ser | Gln | Glu | Arg | |
| | | | | 40 | | | | | 45 | | | | | 50 | | |

| CGG | GAG | ATG | CAG | CGC | GAG | ATC | CTC | TCC | ATT | TTG | GGC | TTG | CCC | CAC | CGC | 249 |
|---|---|---|---|---|---|---|---|---|---|---|---|---|---|---|---|---|
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |

| CCG | CGC | CCG | CAC | CTC | CAG | GGC | AAG | CAC | AAC | TCG | GCA | CCC | ATG | TTC | ATG | 297 |
|---|---|---|---|---|---|---|---|---|---|---|---|---|---|---|---|---|
| Pro | Arg | Pro | His | Leu | Gln | Gly | Lys | His | Asn | Ser | Ala | Pro | Met | Phe | Met | |
| | | 70 | | | | | 75 | | | | | 80 | | | | |

| CTG | GAC | CTG | TAC | AAC | GCC | ATG | GCG | GTG | GAG | GAG | GGC | GGC | GGG | CCC | GGC | 345 |
|---|---|---|---|---|---|---|---|---|---|---|---|---|---|---|---|---|
| Leu | Asp | Leu | Tyr | Asn | Ala | Met | Ala | Val | Glu | Glu | Gly | Gly | Gly | Pro | Gly | |
| | 85 | | | | | 90 | | | | | 95 | | | | | |

| GGC | CAG | GGC | TTC | TCC | TAC | CCC | TAC | AAG | GCC | GTC | TTC | AGT | ACC | CAG | GGC | 393 |
|---|---|---|---|---|---|---|---|---|---|---|---|---|---|---|---|---|
| Gly | Gln | Gly | Phe | Ser | Tyr | Pro | Tyr | Lys | Ala | Val | Phe | Ser | Thr | Gln | Gly | |
| 100 | | | | | 105 | | | | | 110 | | | | | 115 | |

| CCC | CCT | CTG | GCC | AGC | CTG | CAA | GAT | AGC | CAT | TTC | CTC | ACC | GAC | GCC | GAC | 441 |
|---|---|---|---|---|---|---|---|---|---|---|---|---|---|---|---|---|
| Pro | Pro | Leu | Ala | Ser | Leu | Gln | Asp | Ser | His | Phe | Leu | Thr | Asp | Ala | Asp | |
| | | | | 120 | | | | | 125 | | | | | 130 | | |

| ATG | GTC | ATG | AGC | TTC | GTC | AAC | CTC | GTG | GAA | CAT | GAC | AAG | GAA | TTC | TTC | 489 |
|---|---|---|---|---|---|---|---|---|---|---|---|---|---|---|---|---|
| Met | Val | Met | Ser | Phe | Val | Asn | Leu | Val | Glu | His | Asp | Lys | Glu | Phe | Phe | |
| | | | 135 | | | | | 140 | | | | | 145 | | | |

| CAC | CCA | CGC | TAC | CAC | CAT | CGA | GAG | TTC | CGG | TTT | GAT | CTT | TCC | AAG | ATC | 537 |
|---|---|---|---|---|---|---|---|---|---|---|---|---|---|---|---|---|
| His | Pro | Arg | Tyr | His | His | Arg | Glu | Phe | Arg | Phe | Asp | Leu | Ser | Lys | Ile | |
| | | 150 | | | | | 155 | | | | | 160 | | | | |

| CCA | GAA | GGG | GAA | GCT | GTC | ACG | GCA | GCC | GAA | TTC | CGG | ATC | TAC | AAG | GAC | 585 |
|---|---|---|---|---|---|---|---|---|---|---|---|---|---|---|---|---|
| Pro | Glu | Gly | Glu | Ala | Val | Thr | Ala | Ala | Glu | Phe | Arg | Ile | Tyr | Lys | Asp | |
| | 165 | | | | | 170 | | | | | 175 | | | | | |

| TAC | ATC | CGG | GAA | CGC | TTC | GAC | AAT | GAG | ACG | TTC | CGG | ATC | AGC | GTT | TAT | 633 |
|---|---|---|---|---|---|---|---|---|---|---|---|---|---|---|---|---|
| Tyr | Ile | Arg | Glu | Arg | Phe | Asp | Asn | Glu | Thr | Phe | Arg | Ile | Ser | Val | Tyr | |
| 180 | | | | | 185 | | | | | 190 | | | | | 195 | |

| CAG | GTG | CTC | CAG | GAG | CAC | TTG | GGC | AGG | GAA | TCG | GAT | CTC | TTC | CTG | CTC | 681 |
|---|---|---|---|---|---|---|---|---|---|---|---|---|---|---|---|---|
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |

| GAC | AGC | CGT | ACC | CTC | TGG | GCC | TCG | GAG | GAG | GGC | TGG | CTG | GTG | TTT | GAC | 729 |
|---|---|---|---|---|---|---|---|---|---|---|---|---|---|---|---|---|
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |

| ATC | ACA | GCC | ACC | AGC | AAC | CAC | TGG | GTG | GTC | AAT | CCG | CGG | CAC | AAC | CTG | 777 |
|---|---|---|---|---|---|---|---|---|---|---|---|---|---|---|---|---|
| Ile | Thr | Ala | Thr | Ser | Asn | His | Trp | Val | Val | Asn | Pro | Arg | His | Asn | Leu | |
| | | 230 | | | | | 235 | | | | | 240 | | | | |

| GGC | CTG | CAG | CTC | TCG | GTG | GAG | ACG | CTG | GAT | GGG | CAG | AGC | ATC | AAC | CCC | 825 |
|---|---|---|---|---|---|---|---|---|---|---|---|---|---|---|---|---|
| Gly | Leu | Gln | Leu | Ser | Val | Glu | Thr | Leu | Asp | Gly | Gln | Ser | Ile | Asn | Pro | |
| | 245 | | | | | 250 | | | | | 255 | | | | | |

| AAG | TTG | GCG | GGC | CTG | ATT | GGG | CGG | CAC | GGG | CCC | CAG | AAC | AAG | CAG | CCC | 873 |
|---|---|---|---|---|---|---|---|---|---|---|---|---|---|---|---|---|
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |

| TTC | ATG | GTG | GCT | TTC | TTC | AAG | GCC | ACG | GAG | GTC | CAC | TTC | CGC | AGC | ATC | 921 |
|---|---|---|---|---|---|---|---|---|---|---|---|---|---|---|---|---|
| Phe | Met | Val | Ala | Phe | Phe | Lys | Ala | Thr | Glu | Val | His | Phe | Arg | Ser | Ile | |
| | | | | 280 | | | | | 285 | | | | | 290 | | |

| | | |
|---|---|---|
| CGG TCC ACG GGG AGC AAA CAG CGC AGC CAG AAC CGC TCC AAG ACG CCC<br>Arg Ser Thr Gly Ser Lys Gln Arg Ser Gln Asn Arg Ser Lys Thr Pro<br>295 300 305 | | 969 |
| AAG AAC CAG GAA GCC CTG CGG ATG GCC AAC GTG GCA GAG AAC AGC AGC<br>Lys Asn Gln Glu Ala Leu Arg Met Ala Asn Val Ala Glu Asn Ser Ser<br>310 315 320 | | 1017 |
| AGC GAC CAG AGG CAG GCC TGT AAG AAG CAC GAG CTG TAT GTC AGC TTC<br>Ser Asp Gln Arg Gln Ala Cys Lys Lys His Glu Leu Tyr Val Ser Phe<br>325 330 335 | | 1065 |
| CGA GAC CTG GGC TGG CAG GAC TGG ATC ATC GCG CCT GAA GGC TAC GCC<br>Arg Asp Leu Gly Trp Gln Asp Trp Ile Ile Ala Pro Glu Gly Tyr Ala<br>340 345 350 355 | | 1113 |
| GCC TAC TAC TGT GAG GGG GAG TGT GCC TTC CCT CTG AAC TCC TAC ATG<br>Ala Tyr Tyr Cys Glu Gly Glu Cys Ala Phe Pro Leu Asn Ser Tyr Met<br>360 365 370 | | 1161 |
| AAC GCC ACC AAC CAC GCC ATC GTG CAG ACG CTG GTC CAC TTC ATC AAC<br>Asn Ala Thr Asn His Ala Ile Val Gln Thr Leu Val His Phe Ile Asn<br>375 380 385 | | 1209 |
| CCG GAA ACG GTG CCC AAG CCC TGC TGT GCG CCC ACG CAG CTC AAT GCC<br>Pro Glu Thr Val Pro Lys Pro Cys Cys Ala Pro Thr Gln Leu Asn Ala<br>390 395 400 | | 1257 |
| ATC TCC GTC CTC TAC TTC GAT GAC AGC TCC AAC GTC ATC CTG AAG AAA<br>Ile Ser Val Leu Tyr Phe Asp Asp Ser Ser Asn Val Ile Leu Lys Lys<br>405 410 415 | | 1305 |
| TAC AGA AAC ATG GTG GTC CGG GCC TGT GGC TGC CAC TAGCTCCTCC<br>Tyr Arg Asn Met Val Val Arg Ala Cys Gly Cys His<br>420 425 430 | | 1351 |
| GAGAATTCAG ACCCTTTGGG GCCAAGTTTT TCTGGATCCT CCATTGCTCG CCTTGGCCAG | | 1411 |
| GAACCAGCAG ACCAACTGCC TTTTGTGAGA CCTTCCCCTC CCTATCCCCA ACTTTAAAGG | | 1471 |
| TGTGAGAGTA TTAGGAAACA TGAGCAGCAT ATGGCTTTTG ATCAGTTTTT CAGTGGCAGC | | 1531 |
| ATCCAATGAA CAAGATCCTA CAAGCTGTGC AGGCAAAACC TAGCAGGAAA AAAAAACAAC | | 1591 |
| GCATAAAGAA AAATGGCCGG GCCAGGTCAT TGGCTGGGAA GTCTCAGCCA TGCACGGACT | | 1651 |
| CGTTTCCAGA GGTAATTATG AGCGCCTACC AGCCAGGCCA CCCAGCCGTG GGAGGAAGGG | | 1711 |
| GGCGTGGCAA GGGGTGGGCA CATTGGTGTC TGTGCGAAAG GAAAATTGAC CCGGAAGTTC | | 1771 |
| CTGTAATAAA TGTCACAATA AAACGAATGA ATGAAAAAAA AAAAAAAAA A | | 1822 |

(2) INFORMATION FOR SEQ ID NO:17:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:17:

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

```
Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
        210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
        290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

(2) INFORMATION FOR SEQ ID NO:18:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
```

-continued (B) LOCATION: 104..1393
(D) OTHER INFORMATION: /product= "MOP1 (CDNA)"

(xi) SEQUENCE DESCRIPTION: SEQ ID NO:18:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC       115
                                              Met His Val Arg
                                                1

TCG CTG CGC GCT GCG GCG CCA CAC AGC TTC GTG GCG CTC TGG GCG CCT       163
Ser Leu Arg Ala Ala Ala Pro His Ser Phe Val Ala Leu Trp Ala Pro
  5              10                  15                  20

CTG TTC TTG CTG CGC TCC GCC CTG GCC GAT TTC AGC CTG GAC AAC GAG       211
Leu Phe Leu Leu Arg Ser Ala Leu Ala Asp Phe Ser Leu Asp Asn Glu
                 25                  30                  35

GTG CAC TCC AGC TTC ATC CAC CGG CGC CTC CGC AGC CAG GAG CGG CGG       259
Val His Ser Ser Phe Ile His Arg Arg Leu Arg Ser Gln Glu Arg Arg
             40                  45                  50

GAG ATG CAG CGG GAG ATC CTG TCC ATC TTA GGG TTG CCC CAT CGC CCG       307
Glu Met Gln Arg Glu Ile Leu Ser Ile Leu Gly Leu Pro His Arg Pro
         55                  60                  65

CGC CCG CAC CTC CAG GGA AAG CAT AAT TCG GCG CCC ATG TTC ATG TTG       355
Arg Pro His Leu Gln Gly Lys His Asn Ser Ala Pro Met Phe Met Leu
     70                  75                  80

GAC CTG TAC AAC GCC ATG GCG GTG GAG GAG AGC GGG CCG GAC GGA CAG       403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT       451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC       499
Leu Ala Ser Leu Gln Asp Ser His Phe Leu Thr Asp Ala Asp Met Val
            120                 125                 130

ATG AGC TTC GTC AAC CTA GTG GAA CAT GAC AAA GAA TTC TTC CAC CCT       547
Met Ser Phe Val Asn Leu Val Glu His Asp Lys Glu Phe Phe His Pro
        135                 140                 145

CGA TAC CAC CAT CGG GAG TTC CGG TTT GAT CTT TCC AAG ATC CCC GAG       595
Arg Tyr His His Arg Glu Phe Arg Phe Asp Leu Ser Lys Ile Pro Glu
    150                 155                 160

GGC GAA CGG GTG ACC GCA GCC GAA TTC AGG ATC TAT AAG GAC TAC ATC       643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG       691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC       739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA       787
Arg Thr Ile Trp Ala Ser Glu Glu Gly Trp Leu Val Phe Asp Ile Thr
        215                 220                 225

GCC ACC AGC AAC CAC TGG GTG GTC AAC CCT CGG CAC AAC CTG GGC TTA       835
Ala Thr Ser Asn His Trp Val Val Asn Pro Arg His Asn Leu Gly Leu
    230                 235                 240

CAG CTC TCT GTG GAG ACC CTG GAT GGG CAG AGC ATC AAC CCC AAG TTG       883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG       931
Ala Gly Leu Ile Gly Arg His Gly Pro Gln Asn Lys Gln Pro Phe Met
                265                 270                 275
```

```
GTG GCC TTC TTC AAG GCC ACG GAA GTC CAT CTC CGT AGT ATC CGG TCC      979
Val Ala Phe Phe Lys Ala Thr Glu Val His Leu Arg Ser Ile Arg Ser
        280                 285                 290

ACG GGG GGC AAG CAG CGC AGC CAG AAT CGC TCC AAG ACG CCA AAG AAC     1027
Thr Gly Gly Lys Gln Arg Ser Gln Asn Arg Ser Lys Thr Pro Lys Asn
            295                 300                 305

CAA GAG GCC CTG AGG ATG GCC AGT GTG GCA GAA AAC AGC AGC AGT GAC     1075
Gln Glu Ala Leu Arg Met Ala Ser Val Ala Glu Asn Ser Ser Ser Asp
    310                 315                 320

CAG AGG CAG GCC TGC AAG AAA CAT GAG CTG TAC GTC AGC TTC CGA GAC     1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC     1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC     1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC     1267
Thr Asn His Ala Ile Val Gln Thr Leu Val His Phe Ile Asn Pro Asp
    375                 380                 385

ACA GTA CCC AAG CCC TGC TGT GCG CCC ACC CAG CTC AAC GCC ATC TCT     1315
Thr Val Pro Lys Pro Cys Cys Ala Pro Thr Gln Leu Asn Ala Ile Ser
390                 395                 400

GTC CTC TAC TTC GAC GAC AGC TCT AAT GTC ATC CTG AAG AAG TAC AGA     1363
Val Leu Tyr Phe Asp Asp Ser Ser Asn Val Ile Leu Lys Lys Tyr Arg
405                 410                 415                 420

AAC ATG GTG GTC CGG GCC TGT GGC TGC CAC TAGCTCTTCC TGAGACCCTG       1413
Asn Met Val Val Arg Ala Cys Gly Cys His
                425                 430

ACCTTTGCGG GGCCACACCT TTCCAAATCT TCGATGTCTC ACCATCTAAG TCTCTCACTG   1473

CCCACCTTGG CGAGGAGAAC AGACCAACCT CTCCTGAGCC TTCCCTCACC TCCCAACCGG   1533

AAGCATGTAA GGGTTCCAGA AACCTGAGCG TGCAGCAGCT GATGAGCGCC CTTTCCTTCT   1593

GGCACGTGAC GGACAAGATC CTACCAGCTA CCACAGCAAA CGCCTAAGAG CAGGAAAAAT   1653

GTCTGCCAGG AAAGTGTCCA GTGTCCACAT GGCCCCTGGC GCTCTGAGTC TTTGAGGAGT   1713

AATCGCAAGC CTCGTTCAGC TGCAGCGAAA GGAAGGGCTT AGCCAGGGTG GGCGCTGGCG   1773

TCTGTGTTGA AGGGAAACCA AGCAGAAGCC ACTGTAATGA TATGTCACAA TAAAACCCAT   1833

GAATGAAAAA AAAAAAAAAA AAAAAAAAAA AAAAGAATTC                         1873

(2) INFORMATION FOR SEQ ID NO:19:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:19:

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60
```

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Ser Gly
                 85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270

Gln Pro Phe Met Val Ala Phe Phe Lys Ala Thr Glu Val His Leu Arg
        275                 280                 285

Ser Ile Arg Ser Thr Gly Gly Lys Gln Arg Ser Gln Asn Arg Ser Lys
    290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
        355                 360                 365

Tyr Met Asn Ala Thr Asn His Ala Ile Val Gln Thr Leu Val His Phe
    370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
                405                 410                 415

Lys Lys Tyr Arg Asn Met Val Val Arg Ala Cys Gly Cys His
            420                 425                 430

(2) INFORMATION FOR SEQ ID NO:20:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 490..1695

(xi) SEQUENCE DESCRIPTION: SEQ ID NO:20:

```
GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCCTGCGC TGCTCGGACC       180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCCGGT CCTCTCCGTC CAGGAGCCAG       300

GACAGGTGTC GCGCGGCGGG GCTCCAGGGA CCGCGCCTGA GGCCGGCTGC CCGCCCGTCC       360

CGCCCCGCCC CGCCGCCCGC CGCCCGCCGA GCCCAGCCTC CTTGCCGTCG GGGCGTCCCC       420

AGGCCCTGGG TCGGCCGCGG AGCCGATGCG CGCCCGCTGA GCGCCCCAGC TGAGCGCCCC       480

CGGCCTGCC ATG ACC GCG CTC CCC GGC CCG CTC TGG CTC CTG GGC CTG          528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC        576
Ala Leu Cys Ala Leu Gly Gly Gly Gly Pro Gly Leu Arg Pro Pro Pro
 15                  20                  25

GGC TGT CCC CAG CGA CGT CTG GGC GCG CGC GAG CGC CGG GAC GTG CAG        624
Gly Cys Pro Gln Arg Arg Leu Gly Ala Arg Glu Arg Arg Asp Val Gln
 30                  35                  40                  45

CGC GAG ATC CTG GCG GTG CTC GGG CTG CCT GGG CGG CCC CGG CCC CGC        672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG        720
Ala Pro Pro Ala Ala Ser Arg Leu Pro Ala Ser Ala Pro Leu Phe Met
                 65                  70                  75

CTG GAC CTG TAC CAC GCC ATG GCC GGC GAC GAC GAC GAG GAC GGC GCG        768
Leu Asp Leu Tyr His Ala Met Ala Gly Asp Asp Asp Glu Asp Gly Ala
                 80                  85                  90

CCC GCG GAG CGG CGC CTG GGC CGC GCC GAC CTG GTC ATG AGC TTC GTT        816
Pro Ala Glu Arg Arg Leu Gly Arg Ala Asp Leu Val Met Ser Phe Val
                 95                 100                 105

AAC ATG GTG GAG CGA GAC CGT GCC CTG GGC CAC CAG GAG CCC CAT TGG        864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC        912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC        960
Thr Ala Ala Glu Phe Arg Ile Tyr Lys Val Pro Ser Ile His Leu Leu
                145                 150                 155

AAC AGG ACC CTC CAC GTC AGC ATG TTC CAG GTG GTC CAG GAG CAG TCC       1008
Asn Arg Thr Leu His Val Ser Met Phe Gln Val Val Gln Glu Gln Ser
                160                 165                 170

AAC AGG GAG TCT GAC TTG TTC TTT TTG GAT CTT CAG ACG CTC CGA GCT       1056
Asn Arg Glu Ser Asp Leu Phe Phe Leu Asp Leu Gln Thr Leu Arg Ala
175                 180                 185

GGA GAC GAG GGC TGG CTG GTG CTG GAT GTC ACA GCA GCC AGT GAC TGC       1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG       1152
Trp Leu Leu Lys Arg His Lys Asp Leu Gly Leu Arg Leu Tyr Val Glu
                210                 215                 220
```

```
ACT GAG GAC GGG CAC AGC GTG GAT CCT GGC CTG GCC GGC CTG CTG GGT     1200
Thr Glu Asp Gly His Ser Val Asp Pro Gly Leu Ala Gly Leu Leu Gly
            225                 230                 235

CAA CGG GCC CCA CGC TCC CAA CAG CCT TTC GTG GTC ACT TTC TTC AGG     1248
Gln Arg Ala Pro Arg Ser Gln Gln Pro Phe Val Val Thr Phe Phe Arg
            240                 245                 250

GCC AGT CCG AGT CCC ATC CGC ACC CCT CGG GCA GTG AGG CCA CTG AGG     1296
Ala Ser Pro Ser Pro Ile Arg Thr Pro Arg Ala Val Arg Pro Leu Arg
        255                 260                 265

AGG AGG CAG CCG AAG AAA AGC AAC GAG CTG CCG CAG GCC AAC CGA CTC     1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC     1392
Pro Gly Ile Phe Asp Asp Val His Gly Ser His Gly Arg Gln Val Cys
                290                 295                 300

CGT CGG CAC GAG CTC TAC GTC AGC TTC CAG GAC CTC GGC TGG CTG GAC     1440
Arg Arg His Glu Leu Tyr Val Ser Phe Gln Asp Leu Gly Trp Leu Asp
            305                 310                 315

TGG GTC ATC GCT CCC CAA GGC TAC TCG GCC TAT TAC TGT GAG GGG GAG     1488
Trp Val Ile Ala Pro Gln Gly Tyr Ser Ala Tyr Tyr Cys Glu Gly Glu
            320                 325                 330

TGC TCC TTC CCA CTG GAC TCC TGC ATG AAT GCC ACC AAC CAC GCC ATC     1536
Cys Ser Phe Pro Leu Asp Ser Cys Met Asn Ala Thr Asn His Ala Ile
        335                 340                 345

CTG CAG TCC CTG GTG CAC CTG ATG AAG CCA AAC GCA GTC CCC AAG GCG     1584
Leu Gln Ser Leu Val His Leu Met Lys Pro Asn Ala Val Pro Lys Ala
350                 355                 360                 365

TGC TGT GCA CCC ACC AAG CTG AGC GCC ACC TCT GTG CTC TAC TAT GAC     1632
Cys Cys Ala Pro Thr Lys Leu Ser Ala Thr Ser Val Leu Tyr Tyr Asp
                370                 375                 380

AGC AGC AAC AAC GTC ATC CTG CGC AAA CAC CGC AAC ATG GTG GTC AAG     1680
Ser Ser Asn Asn Val Ile Leu Arg Lys His Arg Asn Met Val Val Lys
            385                 390                 395

GCC TGC GGC TGC CAC TGAGTCAGCC CGCCCAGCCC TACTGCAG                 1723
Ala Cys Gly Cys His
            400
```

(2) INFORMATION FOR SEQ ID NO:21:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:21:

```
Met Thr Ala Leu Pro Gly Pro Leu Trp Leu Leu Gly Leu Ala Leu Cys
 1               5                  10                  15

Ala Leu Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
            35                  40                  45

Leu Ala Val Leu Gly Leu Pro Gly Arg Pro Arg Pro Arg Ala Pro Pro
        50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95
```

```
Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
            130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                    165                 170                 175

Ser Asp Leu Phe Phe Leu Asp Leu Gln Thr Leu Arg Ala Gly Asp Glu
                180                 185                 190

Gly Trp Leu Val Leu Asp Val Thr Ala Ala Ser Asp Cys Trp Leu Leu
            195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
                260                 265                 270

Pro Lys Lys Ser Asn Glu Leu Pro Gln Ala Asn Arg Leu Pro Gly Ile
            275                 280                 285

Phe Asp Asp Val His Gly Ser His Gly Arg Gln Val Cys Arg Arg His
            290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
                340                 345                 350

Leu Val His Leu Met Lys Pro Asn Ala Val Pro Lys Ala Cys Cys Ala
            355                 360                 365

Pro Thr Lys Leu Ser Ala Thr Ser Val Leu Tyr Tyr Asp Ser Ser Asn
            370                 375                 380

Asn Val Ile Leu Arg Lys His Arg Asn Met Val Val Lys Ala Cys Gly
385                 390                 395                 400

Cys His (2) INFORMATION FOR SEQ ID NO:22:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 93..1289
        (D) OTHER INFORMATION: /product= "MOP2 CDNA"

(xi) SEQUENCE DESCRIPTION: SEQ ID NO:22:

GCCAGGCACA GGTGCGCCGT CTGGTCCTCC CCGTCTGGCG TCAGCCGAGC CCGACCAGCT      60
```

```
                                                           -continued

ACCAGTGGAT GCGCGCCGGC TGAAAGTCCG AG ATG GCT ATG CGT CCC GGG CCA           113
                                   Met Ala Met Arg Pro Gly Pro
                                    1               5

CTC TGG CTA TTG GGC CTT GCT CTG TGC GCG CTG GGA GGC GGC CAC GGT          161
Leu Trp Leu Leu Gly Leu Ala Leu Cys Ala Leu Gly Gly Gly His Gly
         10              15              20

CCG CGT CCC CCG CAC ACC TGT CCC CAG CGT CGC CTG GGA GCG CGC GAG          209
Pro Arg Pro Pro His Thr Cys Pro Gln Arg Arg Leu Gly Ala Arg Glu
     25              30              35

CGC CGC GAC ATG CAG CGT GAA ATC CTG GCG GTG CTC GGG CTA CCG GGA          257
Arg Arg Asp Met Gln Arg Glu Ile Leu Ala Val Leu Gly Leu Pro Gly
 40              45              50              55

CGG CCC CGA CCC CGT GCA CAA CCC GCG GCT GCC CGG CAG CCA GCG TCC          305
Arg Pro Arg Pro Arg Ala Gln Pro Ala Ala Ala Arg Gln Pro Ala Ser
             60              65              70

GCG CCC CTC TTC ATG TTG GAC CTA TAC CAC GCC ATG ACC GAT GAC GAC          353
Ala Pro Leu Phe Met Leu Asp Leu Tyr His Ala Met Thr Asp Asp Asp
         75              80              85

GAC GGC GGG CCA CCA CAG GCT CAC TTA GGC CGT GCC GAC CTG GTC ATG          401
Asp Gly Gly Pro Pro Gln Ala His Leu Gly Arg Ala Asp Leu Val Met
     90              95             100

AGC TTC GTC AAC ATG GTG GAA CGC GAC CGT ACC CTG GGC TAC CAG GAG          449
Ser Phe Val Asn Met Val Glu Arg Asp Arg Thr Leu Gly Tyr Gln Glu
105             110             115

CCA CAC TGG AAG GAA TTC CAC TTT GAC CTA ACC CAG ATC CCT GCT GGG          497
Pro His Trp Lys Glu Phe His Phe Asp Leu Thr Gln Ile Pro Ala Gly
120             125             130             135

GAG GCT GTC ACA GCT GCT GAG TTC CGG ATC TAC AAA GAA CCC AGC ACC          545
Glu Ala Val Thr Ala Ala Glu Phe Arg Ile Tyr Lys Glu Pro Ser Thr
             140             145             150

CAC CCG CTC AAC ACA ACC CTC CAC ATC AGC ATG TTC GAA GTG GTC CAA          593
His Pro Leu Asn Thr Thr Leu His Ile Ser Met Phe Glu Val Val Gln
         155             160             165

GAG CAC TCC AAC AGG GAG TCT GAC TTG TTC TTT TTG GAT CTT CAG ACG          641
Glu His Ser Asn Arg Glu Ser Asp Leu Phe Phe Leu Asp Leu Gln Thr
     170             175             180

CTC CGA TCT GGG GAC GAG GGC TGG CTG GTG CTG GAC ATC ACA GCA GCC          689
Leu Arg Ser Gly Asp Glu Gly Trp Leu Val Leu Asp Ile Thr Ala Ala
185             190             195

AGT GAC CGA TGG CTG CTG AAC CAT CAC AAG GAC CTG GGA CTC CGC CTC          737
Ser Asp Arg Trp Leu Leu Asn His His Lys Asp Leu Gly Leu Arg Leu
200             205             210             215

TAT GTG GAA ACC GCG GAT GGG CAC AGC ATG GAT CCT GGC CTG GCT GGT          785
Tyr Val Glu Thr Ala Asp Gly His Ser Met Asp Pro Gly Leu Ala Gly
             220             225             230

CTG CTT GGA CGA CAA GCA CCA CGC TCC AGA CAG CCT TTC ATG GTA ACC          833
Leu Leu Gly Arg Gln Ala Pro Arg Ser Arg Gln Pro Phe Met Val Thr
         235             240             245

TTC TTC AGG GCC AGC CAG AGT CCT GTG CGG GCC CCT CGG GCA GCG AGA          881
Phe Phe Arg Ala Ser Gln Ser Pro Val Arg Ala Pro Arg Ala Ala Arg
     250             255             260

CCA CTG AAG AGG AGG CAG CCA AAG AAA ACG AAC GAG CTT CCG CAC CCC          929
Pro Leu Lys Arg Arg Gln Pro Lys Lys Thr Asn Glu Leu Pro His Pro
265             270             275

AAC AAA CTC CCA GGG ATC TTT GAT GAT GGC CAC GGT TCC CGC GGC AGA          977
Asn Lys Leu Pro Gly Ile Phe Asp Asp Gly His Gly Ser Arg Gly Arg
280             285             290             295

GAG GTT TGC CGC AGG CAT GAG CTC TAC GTC AGC TTC CGT GAC CTT GGC         1025
Glu Val Cys Arg Arg His Glu Leu Tyr Val Ser Phe Arg Asp Leu Gly
             300             305             310
```

```
TGG CTG GAC TGG GTC ATC GCC CCC CAG GGC TAC TCT GCC TAT TAC TGT      1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC      1121
Glu Gly Glu Cys Ala Phe Pro Leu Asp Ser Cys Met Asn Ala Thr Asn
            330                 335                 340

CAT GCC ATC TTG CAG TCT CTG GTG CAC CTG ATG AAG CCA GAT GTT GTC      1169
His Ala Ile Leu Gln Ser Leu Val His Leu Met Lys Pro Asp Val Val
            345                 350                 355

CCC AAG GCA TGC TGT GCA CCC ACC AAA CTG AGT GCC ACC TCT GTG CTG      1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG      1265
Tyr Tyr Asp Ser Ser Asn Asn Val Ile Leu Arg Lys His Arg Asn Met
                380                 385                 390

GTG GTC AAG GCC TGT GGC TGC CAC TGAGGCCCCG CCCAGCATCC TGCTTCTACT     1319
Val Val Lys Ala Cys Gly Cys His
            395

ACCTTACCAT CTGGCCGGGC CCCTCTCCAG AGGCAGAAAC CCTTCTATGT TATCATAGCT   1379

CAGACAGGGG CAATGGGAGG CCCTTCACTT CCCCTGGCCA CTTCCTGCTA AAATTCTGGT   1439

CTTTCCCAGT TCCTCTGTCC TTCATGGGGT TTCGGGGCTA TCACCCCGCC CTCTCCATCC   1499

TCCTACCCCA AGCATAGACT GAATGCACAC AGCATCCCAG AGCTATGCTA ACTGAGAGGT   1559

CTGGGGTCAG CACTGAAGGC CCACATGAGG AAGACTGATC CTTGGCCATC CTCAGCCCAC   1619

AATGGCAAAT TCTGGATGGT CTAAGAAGGC CGTGGAATTC TAAACTAGAT GATCTGGGCT   1679

CTCTGCACCA TTCATTGTGG CAGTTGGGAC ATTTTTAGGT ATAACAGACA CATACACTTA   1739

GATCAATGCA TCGCTGTACT CCTTGAAATC AGAGCTAGCT TGTTAGAAAA AGAATCAGAG   1799

CCAGGTATAG CGGTGCATGT CATTAATCCC AGCGCTAAAG AGACAGAGAC AGGAGAATCT   1859

CTGTGAGTTC AAGGCCACAT AGAAAGAGCC TGTCTCGGGA GCAGGAAAAA AAAAAAAAC    1919

GGAATTC                                                            1926

(2) INFORMATION FOR SEQ ID NO:23:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:23:

Met Ala Met Arg Pro Gly Pro Leu Trp Leu Leu Gly Leu Ala Leu Cys
1               5                   10                  15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
        50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
            100                 105                 110
```

```
Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
            130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Ala Asp Gly His Ser
            210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
            275                 280                 285

Gly His Gly Ser Arg Gly Arg Glu Val Cys Arg Arg His Glu Leu Tyr
            290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
            355                 360                 365

Leu Ser Ala Thr Ser Val Leu Tyr Tyr Asp Ser Ser Asn Asn Val Ile
370                 375                 380

Leu Arg Lys His Arg Asn Met Val Val Lys Ala Cys Gly Cys His
385                 390                 395
```

(2) INFORMATION FOR SEQ ID NO:24:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1365

(xi) SEQUENCE DESCRIPTION: SEQ ID NO:24:

```
ATG TCG GGA CTG CGA AAC ACC TCG GAG GCC GTT GCA GTG CTC GCC TCC        48
Met Ser Gly Leu Arg Asn Thr Ser Glu Ala Val Ala Val Leu Ala Ser
1               5                   10                  15

CTG GGA CTC GGA ATG GTT CTG CTC ATG TTC GTG GCG ACC ACG CCG CCG        96
Leu Gly Leu Gly Met Val Leu Leu Met Phe Val Ala Thr Thr Pro Pro
                20                  25                  30
```

```
GCC GTT GAG GCC ACC CAG TCG GGG ATT TAC ATA GAC AAC GGC AAG GAC      144
Ala Val Glu Ala Thr Gln Ser Gly Ile Tyr Ile Asp Asn Gly Lys Asp
         35                  40                  45

CAG ACG ATC ATG CAC AGA GTG CTG AGC GAG GAC GAC AAG CTG GAC GTC      192
Gln Thr Ile Met His Arg Val Leu Ser Glu Asp Asp Lys Leu Asp Val
    50                  55                  60

TCG TAC GAG ATC CTC GAG TTC CTG GGC ATC GCC GAA CGG CCG ACG CAC      240
Ser Tyr Glu Ile Leu Glu Phe Leu Gly Ile Ala Glu Arg Pro Thr His
65                  70                  75                  80

CTG AGC AGC CAC CAG TTG TCG CTG AGG AAG TCG GCT CCC AAG TTC CTG      288
Leu Ser Ser His Gln Leu Ser Leu Arg Lys Ser Ala Pro Lys Phe Leu
             85                  90                  95

CTG GAC GTC TAC CAC CGC ATC ACG GCG GAG GAG GGT CTC AGC GAT CAG      336
Leu Asp Val Tyr His Arg Ile Thr Ala Glu Glu Gly Leu Ser Asp Gln
                100                 105                 110

GAT GAG GAC GAC GAC TAC GAA CGC GGC CAT CGG TCC AGG AGG AGC GCC      384
Asp Glu Asp Asp Asp Tyr Glu Arg Gly His Arg Ser Arg Arg Ser Ala
            115                 120                 125

GAC CTC GAG GAG GAT GAG GGC GAG CAG CAG AAG AAC TTC ATC ACC GAC      432
Asp Leu Glu Glu Asp Glu Gly Glu Gln Gln Lys Asn Phe Ile Thr Asp
    130                 135                 140

CTG GAC AAG CGG GCC ATC GAC GAG AGC GAC ATC ATC ATG ACC TTC CTG      480
Leu Asp Lys Arg Ala Ile Asp Glu Ser Asp Ile Ile Met Thr Phe Leu
145                 150                 155                 160

AAC AAG CGC CAC CAC AAT GTG GAC GAA CTG CGT CAC GAG CAC GGC CGT      528
Asn Lys Arg His His Asn Val Asp Glu Leu Arg His Glu His Gly Arg
                165                 170                 175

CGC CTG TGG TTC GAC GTC TCC AAC GTG CCC AAC GAC AAC TAC CTG GTG      576
Arg Leu Trp Phe Asp Val Ser Asn Val Pro Asn Asp Asn Tyr Leu Val
            180                 185                 190

ATG GCC GAG CTG CGC ATC TAT CAG AAC GCC AAC GAG GGC AAG TGG CTG      624
Met Ala Glu Leu Arg Ile Tyr Gln Asn Ala Asn Glu Gly Lys Trp Leu
    195                 200                 205

ACC GCC AAC AGG GAG TTC ACC ATC ACG GTA TAC GCC ATT GGC ACC GGC      672
Thr Ala Asn Arg Glu Phe Thr Ile Thr Val Tyr Ala Ile Gly Thr Gly
210                 215                 220

ACG CTG GGC CAG CAC ACC ATG GAG CCG CTG TCC TCG GTG AAC ACC ACC      720
Thr Leu Gly Gln His Thr Met Glu Pro Leu Ser Ser Val Asn Thr Thr
225                 230                 235                 240

GGG GAC TAC GTG GGC TGG TTG GAG CTC AAC GTG ACC GAG GGC CTG CAC      768
Gly Asp Tyr Val Gly Trp Leu Glu Leu Asn Val Thr Glu Gly Leu His
                245                 250                 255

GAG TGG CTG GTC AAG TCG AAG GAC AAT CAT GGC ATC TAC ATT GGA GCA      816
Glu Trp Leu Val Lys Ser Lys Asp Asn His Gly Ile Tyr Ile Gly Ala
            260                 265                 270

CAC GCT GTC AAC CGA CCC GAC CGC GAG GTG AAG CTG GAC GAC ATT GGA      864
His Ala Val Asn Arg Pro Asp Arg Glu Val Lys Leu Asp Asp Ile Gly
    275                 280                 285

CTG ATC CAC CGC AAG GTG GAC GAC GAG TTC CAG CCC TTC ATG ATC GGC      912
Leu Ile His Arg Lys Val Asp Asp Glu Phe Gln Pro Phe Met Ile Gly
290                 295                 300

TTC TTC CGC GGA CCG GAG CTG ATC AAG GCG ACG GCC CAC AGC AGC CAC      960
Phe Phe Arg Gly Pro Glu Leu Ile Lys Ala Thr Ala His Ser Ser His
305                 310                 315                 320

CAC AGG AGC AAG CGA AGC GCC AGC CAT CCA CGC AAG CGC AAG AAG TCG     1008
His Arg Ser Lys Arg Ser Ala Ser His Pro Arg Lys Arg Lys Lys Ser
                325                 330                 335

GTG TCG CCC AAC AAC GTG CCG CTG CTG GAA CCG ATG GAG AGC ACG CGC     1056
Val Ser Pro Asn Asn Val Pro Leu Leu Glu Pro Met Glu Ser Thr Arg
```

```
                    340                 345                 350
AGC TGC CAG ATG CAG ACC CTG TAC ATA GAC TTC AAG GAT CTG GGC TGG        1104
Ser Cys Gln Met Gln Thr Leu Tyr Ile Asp Phe Lys Asp Leu Gly Trp
            355                 360                 365

CAT GAC TGG ATC ATC GCA CCA GAG GGC TAT GGC GCC TTC TAC TGC AGC        1152
His Asp Trp Ile Ile Ala Pro Glu Gly Tyr Gly Ala Phe Tyr Cys Ser
370                 375                 380

GGC GAG TGC AAT TTC CCG CTC AAT GCG CAC ATG AAC GCC ACG AAC CAT        1200
Gly Glu Cys Asn Phe Pro Leu Asn Ala His Met Asn Ala Thr Asn His
385                 390                 395                 400

GCG ATC GTC CAG ACC CTG GTC CAC CTG CTG GAG CCC AAG AAG GTG CCC        1248
Ala Ile Val Gln Thr Leu Val His Leu Leu Glu Pro Lys Lys Val Pro
            405                 410                 415

AAG CCC TGC TGC GCT CCG ACC AGG CTG GGA GCA CTA CCC GTT CTG TAC        1296
Lys Pro Cys Cys Ala Pro Thr Arg Leu Gly Ala Leu Pro Val Leu Tyr
            420                 425                 430

CAC CTG AAC GAC GAG AAT GTG AAC CTG AAA AAG TAT AGA AAC ATG ATT        1344
His Leu Asn Asp Glu Asn Val Asn Leu Lys Lys Tyr Arg Asn Met Ile
            435                 440                 445

GTG AAA TCC TGC GGG TGC CAT TGA                                        1368
Val Lys Ser Cys Gly Cys His
    450                 455

(2) INFORMATION FOR SEQ ID NO:25:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:25:

Met Ser Gly Leu Arg Asn Thr Ser Glu Ala Val Ala Val Leu Ala Ser
1               5                   10                  15

Leu Gly Leu Gly Met Val Leu Leu Met Phe Val Ala Thr Thr Pro Pro
                20                  25                  30

Ala Val Glu Ala Thr Gln Ser Gly Ile Tyr Ile Asp Asn Gly Lys Asp
            35                  40                  45

Gln Thr Ile Met His Arg Val Leu Ser Glu Asp Lys Leu Asp Val
    50                  55                  60

Ser Tyr Glu Ile Leu Glu Phe Leu Gly Ile Ala Glu Arg Pro Thr His
65                  70                  75                  80

Leu Ser Ser His Gln Leu Ser Leu Arg Lys Ser Ala Pro Lys Phe Leu
                85                  90                  95

Leu Asp Val Tyr His Arg Ile Thr Ala Glu Glu Gly Leu Ser Asp Gln
                100                 105                 110

Asp Glu Asp Asp Tyr Glu Arg Gly His Arg Ser Arg Arg Ser Ala
            115                 120                 125

Asp Leu Glu Glu Asp Glu Gly Glu Gln Gln Lys Asn Phe Ile Thr Asp
    130                 135                 140

Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Asn Tyr Leu Val
            180                 185                 190

Met Ala Glu Leu Arg Ile Tyr Gln Asn Ala Asn Glu Gly Lys Trp Leu
```

-continued

```
                  195                 200                 205
Thr Ala Asn Arg Glu Phe Thr Ile Thr Val Tyr Ala Ile Gly Thr Gly
            210                 215                 220

Thr Leu Gly Gln His Thr Met Glu Pro Leu Ser Ser Val Asn Thr Thr
225                 230                 235                 240

Gly Asp Tyr Val Gly Trp Leu Glu Leu Asn Val Thr Glu Gly Leu His
            245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
            275                 280                 285

Leu Ile His Arg Lys Val Asp Asp Glu Phe Gln Pro Phe Met Ile Gly
            290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
            325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
            355                 360                 365

His Asp Trp Ile Ile Ala Pro Glu Gly Tyr Gly Ala Phe Tyr Cys Ser
            370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
            405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
            435                 440                 445

Val Lys Ser Cys Gly Cys His
450                 455

(2) INFORMATION FOR SEQ ID NO:26:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /label= BMP3

(xi) SEQUENCE DESCRIPTION: SEQ ID NO:26:

Cys Ala Arg Arg Tyr Leu Lys Val Asp Phe Ala Asp Ile Gly Trp Ser
1               5                  10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
            35                  40                  45

Thr Ile Gln Ser Ile Val Ala Arg Ala Val Gly Val Val Pro Gly Ile
        50                  55                  60
```

```
Pro Glu Pro Cys Cys Val Pro Glu Lys Met Ser Ser Leu Ser Ile Leu
65                  70                  75                  80

Phe Phe Asp Glu Asn Lys Asn Val Val Leu Lys Val Tyr Pro Asn Met
                85                  90                  95

Thr Val Glu Ser Cys Ala Cys Arg
            100
```

(2) INFORMATION FOR SEQ ID NO:27:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= BMP5

(xi) SEQUENCE DESCRIPTION: SEQ ID NO:27:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Leu Met Phe Pro Asp His Val Pro Lys
50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100
```

(2) INFORMATION FOR SEQ ID NO:28:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= BMP6

(xi) SEQUENCE DESCRIPTION: SEQ ID NO:28:

```
Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
                20                  25                  30

Glu Cys Ser Phe Pro Leu Asn Ala His Met Asn Ala Thr Asn His Ala
            35                  40                  45

Ile Val Gln Thr Leu Val His Leu Met Asn Pro Glu Tyr Val Pro Lys
50                  55                  60
```

```
Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Trp Met Val Val
                85                  90                  95

Arg Ala Cys Gly Cys His
                100
```

(2) INFORMATION FOR SEQ ID NO:29:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= OPX
            /note= "WHEREIN XAA AT EACH POS'N IS INDEPENDENTLY
            SELECTED FROM THE RESIDUES OCCURING AT THE CORRESPONDING
            POS'N IN THE C-TERMINAL SEQUENCE OF MOUSE OR HUMAN OP1 OR OP2 (SEQ. ID NOS.5,6,7&8 OR 16,18, 20&22"

(xi) SEQUENCE DESCRIPTION: SEQ ID NO:29:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

(2) INFORMATION FOR SEQ ID NO:30:

(i) SEQUENCE CHARACTERISTICS:
(A) LENGTH: 97 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..97
(D) OTHER INFORMATION: /label= GENERIC-SEQ-5
/note= "WHEREIN EACH XAA IS INDEPENDENTLY SELECTED FROM A GROUP OF ONE OR MORE SPECIFIED AMINO ACIDS AS DEFINED IN THE SPECIFICATION"

(xi) SEQUENCE DESCRIPTION: SEQ ID NO:30:

```
Leu Xaa Xaa Xaa Phe Xaa Xaa Xaa Gly Trp Xaa Xaa Trp Xaa Xaa Xaa
1               5                   10                  15

Pro Xaa Xaa Xaa Xaa Ala Xaa Tyr Cys Xaa Gly Xaa Cys Xaa Xaa Pro
            20                  25                  30
```

```
Xaa Xaa Xaa Xaa Xaa Xaa Xaa Xaa Asn His Ala Xaa Xaa Xaa Xaa Xaa
                35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
            85                  90                  95

Xaa (2) INFORMATION FOR SEQ ID NO:31:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= GENERIC-SEQ-6
            /note= "WHEREIN EACH XAA IS INDEPENDENTLY SELECTED FROM A
            GROUP OF ONE OR MORE SPECIFIED AMINO ACIDS AS DEFINED IN
            THE SPECIFICATION"

(xi) SEQUENCE DESCRIPTION: SEQ ID NO:31:

Cys Xaa Xaa Xaa Xaa Leu Xaa Xaa Xaa Xaa Phe Xaa Xaa Xaa Gly Trp Xaa
1               5                   10                  15

Xaa Trp Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
            85                  90                  95

Xaa Xaa Cys Xaa Cys Xaa
            100

(2) INFORMATION FOR SEQ ID NO:32:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 84..1199
        (D) OTHER INFORMATION: /product= "GDF-1"

(xi) SEQUENCE DESCRIPTION: SEQ ID NO:32:

GGGGACACCG GCCCCGCCCT CAGCCCACTG GTCCCGGGCC GCCGCGGACC CTGCGCACTC      60

TCTGGTCATC GCCTGGGAGG AAG ATG CCA CCG CCG CAG CAA GGT CCC TGC         110
                         Met Pro Pro Pro Gln Gln Gly Pro Cys
                         1               5
```

-continued

```
GGC CAC CAC CTC CTC CTC CTC CTG GCC CTG CTG CTG CCC TCG CTG CCC         158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG         206
Leu Thr Arg Ala Pro Val Pro Pro Gly Pro Ala Ala Ala Leu Leu Gln
             30                  35                  40

GCT CTA GGA CTG CGC GAT GAG CCC CAG GGT GCC CCC AGG CTC CGG CCG         254
Ala Leu Gly Leu Arg Asp Glu Pro Gln Gly Ala Pro Arg Leu Arg Pro
                 45                  50                  55

GTT CCC CCG GTC ATG TGG CGC CTG TTT CGA CGC CGG GAC CCC CAG GAG         302
Val Pro Pro Val Met Trp Arg Leu Phe Arg Arg Arg Asp Pro Gln Glu
                     60                  65                  70

ACC AGG TCT GGC TCG CGG CGG ACG TCC CCA GGG GTC ACC CTG CAA CCG         350
Thr Arg Ser Gly Ser Arg Arg Thr Ser Pro Gly Val Thr Leu Gln Pro
         75                  80                  85

TGC CAC GTG GAG GAG CTG GGG GTC GCC GGA AAC ATC GTG CGC CAC ATC         398
Cys His Val Glu Glu Leu Gly Val Ala Gly Asn Ile Val Arg His Ile
 90                  95                 100                 105

CCG GAC CGC GGT GCG CCC ACC CGG GCC TCG GAG CCT GTC TCG GCC GCG         446
Pro Asp Arg Gly Ala Pro Thr Arg Ala Ser Glu Pro Val Ser Ala Ala
                    110                 115                 120

GGG CAT TGC CCT GAG TGG ACA GTC GTC TTC GAC CTG TCG GCT GTG GAA         494
Gly His Cys Pro Glu Trp Thr Val Val Phe Asp Leu Ser Ala Val Glu
                125                 130                 135

CCC GCT GAG CGC CCG AGC CGG GCC CGC CTG GAG CTG CGT TTC GCG GCG         542
Pro Ala Glu Arg Pro Ser Arg Ala Arg Leu Glu Leu Arg Phe Ala Ala
            140                 145                 150

GCG GCG GCG GCA GCC CCG GAG GGC GGC TGG GAG CTG AGC GTG GCG CAA         590
Ala Ala Ala Ala Ala Pro Glu Gly Gly Trp Glu Leu Ser Val Ala Gln
155                 160                 165

GCG GGC CAG GGC GCG GGC GCG GAC CCC GGG CCG GTG CTG CTC CGC CAG         638
Ala Gly Gln Gly Ala Gly Ala Asp Pro Gly Pro Val Leu Leu Arg Gln
170                 175                 180                 185

TTG GTG CCC GCC CTG GGG CCG CCA GTG CGC GCG GAG CTG CTG GGC GCC         686
Leu Val Pro Ala Leu Gly Pro Pro Val Arg Ala Glu Leu Leu Gly Ala
                190                 195                 200

GCT TGG GCT CGC AAC GCC TCA TGG CCG CGC AGC CTC CGC CTG GCG CTG         734
Ala Trp Ala Arg Asn Ala Ser Trp Pro Arg Ser Leu Arg Leu Ala Leu
                    205                 210                 215

GCG CTA CGC CCC CGG GCC CCT GCC GCC TGC GCG CGC CTG GCC GAG GCC         782
Ala Leu Arg Pro Arg Ala Pro Ala Ala Cys Ala Arg Leu Ala Glu Ala
            220                 225                 230

TCG CTG CTG CTG GTG ACC CTC GAC CCG CGC CTG TGC CAC CCC CTG GCC         830
Ser Leu Leu Leu Val Thr Leu Asp Pro Arg Leu Cys His Pro Leu Ala
235                 240                 245

CGG CCG CGG CGC GAC GCC GAA CCC GTG TTG GGC GGC GGC CCC GGG GGC         878
Arg Pro Arg Arg Asp Ala Glu Pro Val Leu Gly Gly Gly Pro Gly Gly
250                 255                 260                 265

GCT TGT CGC GCG CGG CGG CTG TAC GTG AGC TTC CGC GAG GTG GGC TGG         926
Ala Cys Arg Ala Arg Arg Leu Tyr Val Ser Phe Arg Glu Val Gly Trp
                270                 275                 280

CAC CGC TGG GTC ATC GCG CCG CGC GGC TTC CTG GCC AAC TAC TGC CAG         974
His Arg Trp Val Ile Ala Pro Arg Gly Phe Leu Ala Asn Tyr Cys Gln
                    285                 290                 295

GGT CAG TGC GCG CTG CCC GTC GCG CTG TCG GGG TCC GGG GGG CCG CCG        1022
Gly Gln Cys Ala Leu Pro Val Ala Leu Ser Gly Ser Gly Gly Pro Pro
            300                 305                 310

GCG CTC AAC CAC GCT GTG CTG CGC GCG CTC ATG CAC GCG GCC GCC CCG        1070
Ala Leu Asn His Ala Val Leu Arg Ala Leu Met His Ala Ala Ala Pro
```

```
              315                 320                 325
GGA GCC GCC GAC CTG CCC TGC TGC GTG CCC GCG CGC CTG TCG CCC ATC        1118
Gly Ala Ala Asp Leu Pro Cys Cys Val Pro Ala Arg Leu Ser Pro Ile
330                 335                 340                 345

TCC GTG CTC TTC TTT GAC AAC AGC GAC AAC GTG GTG CTG CGG CAG TAT        1166
Ser Val Leu Phe Phe Asp Asn Ser Asp Asn Val Val Leu Arg Gln Tyr
                    350                 355                 360

GAG GAC ATG GTG GTG GAC GAG TGC GGC TGC CGC TAACCCGGGG CGGGCAGGGA      1219
Glu Asp Met Val Val Asp Glu Cys Gly Cys Arg
                365                 370

CCCGGGCCCA ACAATAAATG CCGCGTGG                                         1247

(2) INFORMATION FOR SEQ ID NO:33:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:33:

Met Pro Pro Gln Gln Gly Pro Cys Gly His His Leu Leu Leu Leu
 1               5                  10                  15

Leu Ala Leu Leu Leu Pro Ser Leu Pro Leu Thr Arg Ala Pro Val Pro
                20                  25                  30

Pro Gly Pro Ala Ala Leu Leu Gln Ala Leu Gly Leu Arg Asp Glu
        35                  40                  45

Pro Gln Gly Ala Pro Arg Leu Arg Pro Val Pro Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
                100                 105                 110

Arg Ala Ser Glu Pro Val Ser Ala Ala Gly His Cys Pro Glu Trp Thr
            115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
    195                 200                 205

Trp Pro Arg Ser Leu Arg Leu Ala Leu Ala Leu Arg Pro Arg Ala Pro
210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Gly Pro Gly Gly Ala Cys Arg Ala Arg Arg Leu
                260                 265                 270
```

```
                                    -continued

Tyr Val Ser Phe Arg Glu Val Gly Trp His Arg Trp Val Ile Ala Pro
        275             280             285

Arg Gly Phe Leu Ala Asn Tyr Cys Gln Gly Gln Cys Ala Leu Pro Val
    290             295             300

Ala Leu Ser Gly Ser Gly Gly Pro Pro Ala Leu Asn His Ala Val Leu
305             310             315                     320

Arg Ala Leu Met His Ala Ala Ala Pro Gly Ala Ala Asp Leu Pro Cys
                325             330                 335

Cys Val Pro Ala Arg Leu Ser Pro Ile Ser Val Leu Phe Phe Asp Asn
            340             345             350

Ser Asp Asn Val Val Leu Arg Gln Tyr Glu Asp Met Val Val Asp Glu
        355             360             365

Cys Gly Cys Arg
    370
```

MORPHOGEN TREATMENT OF ORGAN IMPLANTS

CROSS REFERENCE RELATIONSHIP TO RELATED APPLICATIONS

This application is a continuation of U.S. Ser. No. 08/152,901, filed Nov. 15, 1993 (now abandoned) which is a continuation of Ser. No. 07/938,337, filed Aug. 28, 1992 (now abandoned) which is a continuation-in-part of (1) U.S. Ser. No. 753,059, filed Aug. 30, 1991 (now abandoned), which is a continuation-in-part of U.S. Ser. No. 667,274, filed Mar. 11, 1991 (now abandoned), (2) U.S. Ser. No. 752,764, filed Aug. 30, 1991 (now abandoned), which is a continuation-in-part of U.S. Ser. No. 667,274, filed Mar. 11, 1991, now abandoned, and (3) U.S. Ser. No. 938,336, filed Aug. 28, 1992, filed on even date herewith, the disclosures of which are incorporated herein by reference (now abandoned).

FIELD OF THE INVENTION

The present invention relates generally to methods and compositions useful in the transplantation of living tissues and organs. More particularly, this invention relates to methods and compositions for enhancing the viability of living tissues and organs to be transplanted.

BACKGROUND OF THE INVENTION

The success of organ or living tissue transplantation depends greatly on the preservation of the tissue activity (e.g., tissue or organ viability) at the time of harvest of the organ from a donor, during storage of the harvested organ, and at transplantation. To date, preservation of organs such as lungs, pancreas, heart and liver remains a significant stumbling block to the successful transplantation of these organs. Tissues and organs for transplantation are subject to the tissue destructive effects associated with the body's inflammatory response, which typically is stimulated in response to an initial tissue injury. Accordingly, organs and tissues to be transplanted are at risk of tissue damage following their removal from a donor, during storage and upon transplantation. It is also currently believed that the tissue damage to transplanted tissue may in large part be due to ischemia-reperfusion injury to the organ after it has been transplanted in the organ recipient.

U.S. Pat. No. 4,952,409 describes a superoxide dismutase-containing liposome to inhibit reperfusion injury. U.S. Pat. No. 5,002,965 describes the use of ginkolides, known platelet activating factor antagonists, to inhibit reperfusion injury. Both of these factors are described as working primarily by inhibiting the release of and/or inhibiting the damaging effects of free oxygen radicals. A number of patents also have issued on the use of immunosuppressants for inhibiting graft rejection. A representative listing includes U.S. Pat. Nos. 5,104,858, 5,008,246 and 5,068,323. A significant problem with many immunosuppressants is their low therapeutic index, requiring the administration of high doses that can have significant toxic side effects.

Therefore, an object of the present invention is to provide compositions and methods for enhancing the viability of mammalian living tissues and organs to be transplanted, including protecting the tissues and organs to be transplanted from immune cell-mediated tissue destruction, including the tissue damage associated with ischemia-reperfusion injury. Another object is to provide a preservation solution for maintaining harvested organs and living tissues that is capable of enhancing the viability of the harvested organs and tissues, including protecting them from tissue damage, particularly immune cell-mediated tissue damage. Still another object is to provide compositions and methods for protecting transplanted tissues and organs from tissue damage, particularly immune cell-mediated tissue damage, including the tissue damage associated with ischemia-reperfusion injury.

These and other objects and features of the invention will be apparent from the description, drawings and claims which follow.

SUMMARY OF THE INVENTION

The present invention provides methods and compositions for enhancing the viability of living tissues and organs to be transplanted in a mammal. The methods and compositions provide to the living tissue or organ to be transplanted a therapeutically effective concentration of a morphogenic protein ("morphogen", as defined herein), sufficient to substantially protect the treated tissue from the tissue destructive effects associated with the inflammatory response.

As embodied herein, the expression "enhance the viability of" living tissues or organs, means protection from, reduction of and/or elimination of reduced or lost tissue or organ function as a result of tissue death, particularly immune cell-mediated tissue death. The expression "protecting" living tissue or organs to be transplanted means substantially inhibiting the tissue damage normally associated with transplantation, particularly immune cell-mediated tissue damage, including regenerating damaged tissue and/or inhibiting original damage thereto. Similarly, the expression "alleviating" means the protection from, reduction of and/or elimination of undesired tissue destruction, particularly immune cell-mediated tissue destruction. The tissue destruction may be in response to an initial tissue injury, which may be mechanical, chemical, biological or immunological in origin. "Transplanted" living tissue encompasses both tissue transplants (e.g., as in the case of bone marrow transplants) and tissue grafts. The term "ischemic-reperfusion injury" refers to the initial damage associated with oxygen deprivation of a cell and the subsequent damage associated with the inflammatory response when the cell is resupplied with oxygen. As embodied herein, the term "hyperoxia-induced injury" refers to the tissue damage associated with prolonged exposure to lethally high doses of oxygen, e.g., greater than 95% $O_2$, including the tissue damage associated with the inflammatory response to the toxic oxygen concentration. Accordingly, as used herein, "toxic oxygen concentrations" refers to the tissue damage associated with the injury induced by both lethally low oxygen concentrations (including a complete lack of oxygen), and by lethally high oxygen concentrations. Finally, a "free oxygen radical inhibiting agent" means a molecule capable of inhibiting the release of, and/or inhibiting the tissue damaging effects of, free oxygen radicals.

In one aspect, the invention features compositions and methods that administer to a mammal a therapeutically effective amount of a morphogenic protein ("morphogen"), as defined herein sufficient to protect a living tissue or organ from the tissue destructive effects associated with the body's inflammatory response.

In another aspect, the invention features compositions and methods that administer to a mammal a compound that stimulates in vivo a therapeutically effective concentration of an endogenous morphogen within the body of the mammal sufficient to protect a living tissue or organ from the tissue destructive effects associated with the inflammatory response. These compounds are referred to herein as morphogen-stimulating agents, and are understood to include substances which, when administered to a mammal, act on cells of tissue(s) or organ(s) that normally are responsible for, or capable of, producing a morphogen and/or secreting a morphogen, and which cause the endogenous level of the morphogen to be altered. The agent may act, for example, by stimulating expression and/or secretion of an endogenous morphogen.

In one embodiment of the invention, the morphogen or morphogen-stimulating agent is provided to the living tissue or organ to be transplanted prior to removal of tissue or organ from the donor. The morphogen or morphogen-stimulating agent may be provided to the donor host directly, as by injection of the compound to the tissue, or indirectly, e.g., by oral or parenteral administration.

Alternatively or, in addition, once removed from the donor, the organ or living tissue is placed in a preservation solution containing a morphogen or morphogen-stimulating agent. In addition, the recipient also preferably is provided with a morphogen or morphogen-stimulating agent just prior to, or concomitant with, transplantation. In all cases, the morphogen or morphogen-stimulating agent may be administered directly to the tissue at risk, as by injection to the tissue, or it may be provided systemically, either by oral or parenteral administration.

The morphogens described herein are envisioned to be useful in enhancing viability of any organ or living tissue to be transplanted. The morphogens may be used to particular advantage in lung, heart, liver, kidney or pancreas transplants, as well as in the transplantation and/or grafting of bone marrow, skin, gastrointestinal mucosa, and other living tissues.

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) *PNAS* 88:4250–4254), all of which are presented in Table II and Seq. ID Nos.5–14), and the recently identified 60A protein (from Drosophila, Seq. ID No. 24, see Wharton et al. (1991) *PNAS* 88:9214–9218.) The members of this family, which include members of the TGF-β super-family of proteins, share substantial amino acid sequence homology in their C-terminal regions. The proteins are translated as a precursor, having an N-terminal signal peptide sequence, typically less than about 30 residues, followed by a "pro" domain that is cleaved to yield the mature sequence. The signal peptide is cleaved rapidly upon translation, at a cleavage site that can be predicted in a given sequence using the method of Von Heijne ((1986) *Nucleic Acids Research* 14:4683–4691.) Table I, below, describes the various morphogens identified to date, including their nomenclature as used herein, their Seq. ID references, and publication sources for the amino acid sequences for the full length proteins not included in the Seq. Listing. The disclosure of these publications is incorporated herein by reference.

TABLE I

| | |
|---|---|
| "OP-1" | Refers generically to the group of morphogenically active proteins expressed from part or all of a DNA sequence encoding OP-1 protein, including allelic |

TABLE I-continued

| | |
|---|---|
| | and species variants thereof, e.g., human OP-1 ("hOP-1", Seq. ID No. 5, mature protein amino acid sequence), or mouse OP-1 ("mOP-1", Seq. ID No. 6, mature protein amino acid sequence.) The conserved seven cysteine skeleton is defined by residues 38 to 139 of Seq. ID Nos. 5 and 6. The cDNA sequences and the amino acids encoding the full length proteins are provided in Seq. Id Nos. 16 and 17 (hOP1) and Seq. ID Nos. 18 and 19 (mOP1.) The mature proteins are defined by residues 293–431 (hOP1, Seq. ID No. 17) and 292–430 (mOP1, Seq. ID No. 19). The "pro" regions of the proteins, cleaved to yield the mature, morphogenically active proteins are defined essentially by residues 30–292 (hOP1, Seq. ID No. 17) and residues 30–291 (mOP1, Seq ID No. 19). |
| "OP-2" | refers generically to the group of active proteins expressed from part or all of a DNA sequence encoding OP-2 protein, including allelic and species variants thereof, e.g., human OP-2 ("hOP-2", Seq. ID No. 7, mature protein amino acid sequence) or mouse OP-2 ("mOP-2", Seq. ID No. 8, mature protein amino acid sequence). The conserved seven cysteine skeleton is defined by residues 38 to 139 of Seq. ID Nos. 7 and 8. The cDNA sequences and the amino acids encoding the full length proteins are provided in Seq. ID Nos. 20 and 21 (hOP2) and Seq. ID Nos. 22 and 23 (mOP2.) The mature proteins are defined essentially by residues 264–402 (hOP2, Seq ID No. 21) and 261–399 (mOP2, Seq. ID No. 23) . The "pro" regions of the proteins, cleaved to yield the mature, morphogenically active proteins likely are defined essentially by and residues 18–263 (hOP2, Seq. ID No. 21) and residues 18–260 (mOP2, Seq. ID No. 23). (Another cleavage site also occurs 21 residues upstream for both OP-2 proteins.) |
| "CBMP2" | refers generically to the morphogenically active proteins expressed from a DNA sequence encoding the CBMP2 proteins, including allelic and species variants thereof, e.g., human CBMP2A ("CBMP2A(fx)", Seq ID No. 9) or human CBMP2B DNA ("CBMP2B(fx)", Seq. ID No. 10). The amino acid sequence for the full length proteins, referred to in the literature as BMP2A and BMP2B, or BMP2 and BMP4, appear in Wozney, et al. (1988) Science 242:1528–1534. The pro domain for BMP2 (BMP2A) likely includes residues 25–248 or 25–282 of the published sequence; the mature protein, residues 249–396 or 283–396 of the published sequence. The pro domain for BMP4 (BMP2B) likely includes residues 25–256 or 25–292 of the published sequence; the mature protein, residues 257–408 or 293–408 of the published sequence. |
| "DPP(fx)" | refers to protein sequences encoded by the Drosophila DPP gene and defining the conserved seven cysteine skeleton (Seq. ID No. 11). The amino acid sequence for the full length protein appears in Padgett, et al (1987) Nature 325: 81–84. The pro domain likely extends from the signal peptide cleavage site to residue 456 of the published sequence; the mature protein likely is defined by residues 457–588, of the published sequence. |
| "Vgl(fx)" | refers to protein sequences encoded by the Xenopus Vgl gene and defining the conserved seven cysteine skeleton (Seq. ID No. 12). The amino acid sequence for the full length protein appears in |

TABLE I-continued

| | |
|---|---|
| | Weeks (1987) Cell 51: 861–867. The prodomain likely extends from the signal peptide cleavage site to residue 246 of the published sequence; the mature protein likely is defined by residues 247–360 of the published sequence. |
| "Vgr-1(fx)" | refers to protein sequences encoded by the murine Vgr-1 gene and defining the conserved seven cysteine skeleton (Seq. ID No. 13). The amino acid sequence for the full length protein appears in Lyons, et al, (1989) PNAS 86: 4554–4558. The prodomain likely extends from the signal peptide cleavage site to residue 299 of the published sequence; the mature protein likely defined by residues 300–438 of the published sequence. |
| "GDF-1(fx)" | refers to protein sequences encoded by the human GDF-1 gene and defining the conserved seven cysteine skeleton (Seq. ID No. 14). The cDNA and encoded amino sequence for the full length protein is provided in Seq. ID. No. 32. The prodomain likely extends from the signal peptide cleavage site to residue 214 of Seq. ID. No. 32; the mature protein likely is defined by residues 215–372 of Seq. ID No. 32. |
| "60A" | refers generically to the morphogenically active proteins expressed from part or all of a DNA sequence (from the Drosophila 60A gene) encoding the 60A proteins (see Seq. ID No. 24 wherein the cDNA and encoded amino acid sequence for the full length protein is provided). "60A(fx)" refers to the protein sequences defining the conserved seven cysteine skeleton (residues 354 to 455 of Seq. ID No. 24.) The prodomain likely extends from the signal peptide cleavage site to residue 324 of Seq. ID No. 24; the mature protein likely is defined by residues 325–455 of Seq. ID No. 24. |
| "BMP3(fx)" | refers to protein sequences encoded by the human BMP3 gene and defining the conserved seven cysteine skeleton (Seq. ID No. 26). The amino acid sequence for the full length protein appears in Wozney et al. (1988) Science 242: 1528–1534. The pro domain likely extends from the signal peptide cleavage site to residue 290 of the published sequence; the mature protein likely is defined by residues 291–472 of the published sequence. |
| "BMP5(fx)" | refers to protein sequences encoded by the human BMP5 gene and defining the conserved seven cysteine skeleton (Seq. ID No. 27). The amino acid sequence for the full length protein appears in Celeste, et al. (1991) PNAS 87: 9843–9847. The pro domain likely extends from the signal peptide cleavage site to residue 316 of the published sequence; the mature protein likely is defined by residues 317–454 of the published sequence. |
| "BMP6(fx)" | refers to protein sequences encoded by the human BMP6 gene and defining the conserved seven cysteine skeleton (Seq. ID No. 28). The amino acid sequence for the full length protein appears in Celeste, et al. (1990) PNAS 87: 9843–5847. The pro domain likely includes extends from the signal peptide cleavage site to residue 374 of the published sequence; the mature sequence likely includes residues 375–513 of the published sequence. |

The OP-2 proteins have an additional cysteine residue in this region (e.g., see residue 41 of Seq. ID Nos. 7 and 8), in addition to the conserved cysteine skeleton in common with the other proteins in this family. The GDF-1 protein has a four amino acid insert within the conserved skeleton (residues 44–47 of Seq. ID No. 14) but this insert likely does not interfere with the relationship of the cysteines in the folded structure. In addition, the CBMP2 proteins (Seq. ID Nos. 9 and 10) are missing one amino acid residue within the cysteine skeleton.

The morphogens are inactive when reduced, but are active as oxidized homodimers and when oxidized in combination with other morphogens described herein (e.g., as heterodimers). Thus, as defined herein, a morphogen is a dimeric protein comprising a pair of polypeptide chains, wherein each polypeptide chain comprises at least the C-terminal six cysteine skeleton defined by residues 43–139 of Seq. ID No. 5, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one preferred aspect, the morphogens of this invention comprise one of two species of generic amino acid sequences: Generic Sequence 1 (Seq. ID No. 1) or Generic Sequence 2 (Seq. ID No. 2); where each Xaa indicates one of the 20 naturally-occurring L-isomer, α-amino acids or a derivative thereof. Generic Sequence 1 comprises the conserved six cysteine skeleton and Generic Sequence 2 comprises the conserved six cysteine skeleton plus the additional cysteine identified in OP-2 (see residue 36, Seq. ID No. 2). In another preferred aspect, these sequences further comprise the following additional sequence at their N-terminus:

```
Cys Xaa Xaa Xaa Xaa  (Seq. ID No. 15)
 1               5
```

Preferred amino acid sequences within the foregoing generic sequences include:. Generic Sequence 3 (Seq. ID No. 3), Generic Sequence 4 (Seq. ID No. 4), Generic Sequence 5 (Seq. ID No. 30) and Generic Sequence 6 (Seq. ID No. 31), listed below. These Generic Sequences accommodate the homologies shared among the various preferred members of this morphogen family identified in Table II, as well as the amino acid sequence variation among them. Specifically, Generic Sequences 3 (Seq. ID No. 3) and 4 (Seq. ID No. 4) are composite amino acid sequences of the following proteins presented in Table II and identified in Seq. ID Nos. 5–14: human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14.) The generic sequences include both the amino acid identity shared by the sequences in Table II, as well as alternative residues for the variable positions within the sequence. Note that these generic sequences allow for an additional cysteine at position 41 or 46 in Generic Sequences 3 (Seq. ID No. 3) or 4

(Seq. ID No. 4), respectively, providing an appropriate cysteine skeleton where inter- or intramolecular disulfide bonds can form, and contain certain critical amino acids which influence the tertiary structure of the proteins.

```
          Generic Sequence 3 (Seq. ID No.3)

Leu Tyr Val Xaa Phe
     1               5

Xaa Xaa Xaa Gly Trp Xaa Xaa Trp Xaa
                 10

Xaa Ala Pro Xaa Gly Xaa Xaa Ala
 15              20

Xaa Tyr Cys Xaa Gly Xaa Cys Xaa
         25              30

Xaa Pro Xaa Xaa Xaa Xaa Xaa
                 35

Xaa Xaa Xaa Asn His Ala Xaa Xaa
             40          45

Xaa Xaa Leu Xaa Xaa Xaa Xaa Xaa
             50

Xaa Xaa Xaa Xaa Xaa Xaa Xaa Cys
         55                  60

Cys Xaa Pro Xaa Xaa Xaa Xaa Xaa
                 65

Xaa Xaa Xaa Leu Xaa Xaa Xaa
 70              75

Xaa Xaa Xaa Xaa Val Xaa Leu Xaa
                 80

Xaa Xaa Xaa Xaa Met Xaa Val Xaa
 85                      90

Xaa Cys Gly Cys Xaa
         95
``` wherein each Xaa of Genetic Sequence 3 (Seq. ID No. 3) is independently selected from a group of one or more specified amino acids defined as follows: "Res." means "residue" and Xaa at res.4=(Ser, Asp or Glu); Xaa at res.6=(Arg, Gln, Ser or Lys); Xaa at res.7=(Asp or Glu); Xaa at res.8=(Leu or Val); Xaa at res.11=(Gln, Leu, Asp, His or Asn); Xaa at res.12=(Asp, Arg or Asn); Xaa at res.14=(Ile or Val); Xaa at res.15=(Ile or Val); Xaa at res.18=(Glu, Gln, Leu, Lys, Pro or Arg); Xaa at res.20=(Tyr or Phe); Xaa at res.21=(Ala, Ser, Asp, Met, His, Leu or Gln); Xaa at res.23=(Tyr, Asn or Phe); Xaa at res.26=(Glu, His, Tyr, Asp or Gln); Xaa at res.28=(Glu, Lys, Asp or Gln); Xaa at res.30=(Ala, Ser, Pro or Gln); Xaa at res.31=(Phe, Leu or Tyr); Xaa at res.33=(Leu or Val); Xaa at res.34=(Asn, Asp, Ala or Thr); Xaa at res.35=(Ser, Asp, Glu, Leu or Ala); Xaa at res.36=(Tyr, Cys, His, Ser or Ile); Xaa at res.37=(Met, Phe, Gly or Leu); Xaa at res.38=(Asn or Ser); Xaa at res.39=(Ala, Ser or Gly); Xaa at res.40=(Thr, Leu or Ser); Xaa at res.44=(Ile or Val); Xaa at res.45=(Val or Leu); Xaa at res.46=(Gln or Arg); Xaa at res.47=(Thr, Ala or Ser); Xaa at res.49=(Val or Met); Xaa at res.50=(His or Asn); Xaa at res.51=(Phe, Leu, Asn, Ser, Ala or Val); Xaa at res.52=(Ile, Met, Asn, Ala or Val); Xaa at res.53=(Asn, Lys, Ala or Glu); Xaa at res.54=(Pro or Ser); Xaa at res.55=(Glu, Asp, Asn, or Gly); Xaa at res.56=(Thr, Ala, Val, Lys, Asp, Tyr, Ser or Ala); Xaa at res.57=(Val, Ala or Ile); Xaa at res.58=(Pro or Asp); Xaa at res.59=(Lys or Leu); Xaa at res.60=(Pro or Ala); Xaa at res.63=(Ala or Val); Xaa at res.65=(Thr or Ala); Xaa at res.66=(Gln, Lys, Arg or Glu); Xaa at res.67=(Leu, Met or Val); Xaa at res.68=(Asn, Ser or Asp); Xaa at res.69=(Ala, Pro or Ser); Xaa at res.70=(Ile, Thr or Val); Xaa at res.71=(Ser or Ala); Xaa at res.72=(Val or Met); Xaa at res.74=(Tyr or Phe); Xaa at res.75=(Phe, Tyr or Leu); Xaa at res.76=(Asp or Asn); Xaa at res.77=(Asp, Glu, Asn or Ser); Xaa at res.78=(Ser, Gln, Asn or Tyr); Xaa at res.79=(Ser, Asn, Asp or Glu); Xaa at res.80=(Asn, Thr or Lys); Xaa at res.82=(Ile or Val); Xaa at res.84=(Lys or Arg); Xaa at res.85=(Lys, Asn, Gln or His); Xaa at res.86=(Tyr or His); Xaa at res.87=(Arg, Gln or Glu); Xaa at res.88=(Asn, Glu or Asp); Xaa at res.90=(Val, Thr or Ala); Xaa at res.92=(Arg, Lys, Val, Asp or Glu); Xaa at res.93=(Ala, Gly or Glu); and Xaa at res.97=(His or Arg);

Generic Sequence 4 (Seq. ID No.4)

```
Cys Xaa Xaa Xaa Xaa Leu Tyr Val Xaa Phe
 1               5                   10

Xaa Xaa Xaa Gly Trp Xaa Xaa Trp Xaa
                15

Xaa Ala Pro Xaa Gly Xaa Xaa Ala
 20                 25

Xaa Tyr Cys Xaa Gly Xaa Cys Xaa
        30                  35

Xaa Pro Xaa Xaa Xaa Xaa Xaa
                40

Xaa Xaa Xaa Asn His Ala Xaa Xaa
        45                  50

Xaa Xaa Leu Xaa Xaa Xaa Xaa Xaa
                55

Xaa Xaa Xaa Xaa Xaa Xaa Xaa Cys
     60                 65

Cys Xaa Pro Xaa Xaa Xaa Xaa Xaa
            70

Xaa Xaa Xaa Leu Xaa Xaa Xaa
 75                 80

Xaa Xaa Xaa Xaa Val Xaa Leu Xaa
            85

Xaa Xaa Xaa Xaa Met Xaa Val Xaa
 90                 95

Xaa Cys Gly Cys Xaa
        100
``` wherein each Xaa of Genetic Sequence 4 (Seq. ID No. 4) is independently selected from a group of one or more specified amino acids as defined by the following: "Res." means "residue" and Xaa at res.2=(Lys or Arg); Xaa at res.3=(Lys or Arg); Xaa at res.4=(His or Arg); Xaa at res.5=(Glu, Ser. His, Gly, Arg or Pro); Xaa at res.9=(Ser, Asp or Glu); Xaa at res.11=(Arg, Gln, Ser or Lys); Xaa at res.12=(Asp or Glu); Xaa at res.13=(Leu or Val); Xaa at res.16=(Gln, Leu, Asp, His or Asn); Xaa at res.17=(Asp, Arg, or Asn); Xaa at res.19=(Ile or Val); Xaa at res.20=(Ile or Val); Xaa at res.23=(Glu, Gln, Leu, Lys, Pro or Arg); Xaa at res.25=(Tyr or Phe); Xaa at res.26=(Ala, Ser, Asp, Met, His, Leu, or Gln); Xaa at res.28=(Tyr, Asn or Phe); Xaa at res.31=(Glu, His, Tyr, Asp or Gln); Xaa at res.33=Glu, Lys, Asp or Gln); Xaa at res.35=(Ala, Ser or Pro); Xaa at res.36=(Phe, Leu or Tyr); Xaa at res.38=(Leu or Val); Xaa at res.39=(Asn, Asp, Ala or Thr); Xaa at res.40=(Ser, Asp, Glu, Leu or Ala); Xaa at res.41=(Tyr, Cys, His, Ser or Ile); Xaa at res.42=(Met, Phe, Gly or Leu); Xaa at res.44=(Ala, Ser or Gly); Xaa at res.45=(Thr, Leu or Ser); Xaa at res.49=(Ile or Val); Xaa at res.50=(Val or Leu); Xaa at res.51=(Gln or Arg); Xaa at res.52=(Thr, Ala or Ser); Xaa at res.54=(Val or Met); Xaa at res.55=(His or Asn); Xaa at res.56=(Phe, Leu, Asn, Ser, Ala or Val); Xaa at res.57=(Ile, Met, Asn, Ala or Val); Xaa at res.58=(Asn, Lys, Ala or Glu); Xaa at res.59=(Pro or Ser); Xaa at res.60=(Glu, Asp, or Gly); Xaa at res.61=(Thr, Ala, Val, Lys, Asp, Tyr, Ser or Ala); Xaa at res.62=(Val, Ala or Ile); Xaa at res.63=(Pro or Asp); Xaa at res.64=(Lys or Leu); Xaa at res.65=(Pro or Ala); Xaa at res.68=(Ala or Val); Xaa at res.70=(Thr or Ala); Xaa at res.71=(Gln, Lys, Arg or Glu); Xaa at res.72=(Leu, Met or Val); Xaa at res.73=(Asn, Ser or Asp); Xaa at res.74=(Ala, Pro or Ser); Xaa at res.75(Ile, Thr or Val); Xaa at res.76=(Ser or Ala); Xaa at res.77=(Val or Met); Xaa at res.79=(Tyr or Phe); Xaa at res.80=(Phe, Tyr or Leu); Xaa at res.81=(Asp or Asn); Xaa at res.82=(Asp, Glu, Asn or Ser); Xaa at res.83=(Ser, Gln, Asn or Tyr); Xaa at res.84=(Ser, Asn, Asp or Glu); Xaa at res.85=(Asn, Thr or Lys); Xaa at res.87=(Ile or Val); Xaa at res.89=(Lys or Arg); Xaa at res.90=(Lys, Asn, Gln or His); Xaa at res.91=(Tyr or His); Xaa at res.92=(Arg, Gln or Glu); Xaa at res.93=(Asn, Glu or Asp); Xaa at res.95=(Val, Thr or Ala); Xaa at res.97=(Arg, Lys, Val, Asp or Glu); Xaa at res.98=(Ala, Gly or Glu); and Xaa at res.102=(His or Arg).

Similarly, Generic Sequence 5 (Seq. ID No. 30) and Generic Sequence 6 (Seq. ID No. 31) accommodate the homologies shared among all the morphogen protein family members identified in Table II. Specifically, Generic Sequences 5 and 6 are composite amino acid sequences of human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–22), CBMP2A (Seq. ID No. 9), CBMP2B (Seq. ID No. 10), DPP (from Drosophila, Seq. ID No. 11), Vgl, (from Xenopus, Seq. ID No. 12), Vgr-1 (from mouse, Seq. ID No. 13), and GDF-1 (from mouse, Seq. ID No. 14), human BMP3 (Seq. ID No. 26), human BMP5 (Seq. ID No. 27), human BMP6 (Seq. ID No. 28) and 60(A) (from Drosophila, Seq. ID Nos. 24–25). The generic sequences include both the amino acid identity shared by these sequences in the C-terminal domain, defined by the six and seven cysteine skeletons (Generic Sequences 5 and 6, respectively), as well as alternative residues for the variable positions within the sequence. As for Generic Sequences 3 and 4 (Seq. ID No. 3 and 4), Generic Sequences 5 and 6 (Seq. ID No. 30 and 31)allow for an additional cysteine at position 41 (Generic Sequence 5, Seq. ID No. 30) or position 46 (Generic Sequence 6, Seq. ID No. 31), providing an appropriate cysteine skeleton where inter- or intramolecular disulfide bonds can form, and containing certain critical amino acids which influence the tertiary structure of the proteins.

```
        Generic Sequence 5 (Seq. ID No.30)

Leu Xaa Xaa Xaa Phe
    1               5

Xaa Xaa Xaa Gly Trp Xaa Xaa Trp Xaa
                10

Xaa Xaa Pro Xaa Xaa Xaa Xaa Ala
    15                  20

Xaa Tyr Cys Xaa Gly Xaa Cys Xaa
        25                  30

Xaa Pro Xaa Xaa Xaa Xaa Xaa
                35

Xaa Xaa Xaa Asn His Ala Xaa Xaa
```

```
                    -continued
            40                      45

Xaa Xaa Xaa Xaa Xaa Xaa Xaa Xaa
                50

Xaa Xaa Xaa Xaa Xaa Xaa Xaa Cys
    55                      60

Cys Xaa Pro Xaa Xaa Xaa Xaa
                65

Xaa Xaa Xaa Leu Xaa Xaa Xaa
    70                  75

Xaa Xaa Xaa Xaa Val Xaa Leu Xaa
                80

Xaa Xaa Xaa Xaa Met Xaa Val Xaa
    85                      90

Xaa Cys Xaa Cys Xaa
            95
``` wherein each Xaa of Generic Sequence 5 (Seq. ID No. 30) is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp, Glu or Lys); Xaa at res.8=(Leu, Val or Ile); Xaa at res.11=(Gln, Leu, Asp, His, Asn or Ser); Xaa at res.12=(Asp, Arg, Asn or Glu); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln or Ser); Xaa at res.28=(Glu, Lys, Asp, Gln or Ala); Xaa at res.30=(Ala, Ser, Pro, Gln or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38= (Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val or Leu); Xaa at res.53=(Asn, Lys, Ala, Glu, Gly or Phe); Xaa at res.54=(Pro, Ser or Val); Xaa at res.55=(Glu, Asp, Asn, Gly, Val or Lys); Xaa at res.56=(Thr, Ala, Val, Lys, Asp, Tyr, Ser, Ala, Pro or His); Xaa at res.57=(Val, Ala or Ile); Xaa at res.58=(Pro or Asp); Xaa at res.59=(Lys, Leu or Glu); Xaa at res.60=(Pro or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His or Val); Xaa at res.86=(Tyr or His); Xaa at res.87=(Arg, Gln, Glu or Pro); Xaa at res.88=(Asn, Glu or Asp); Xaa at res.90=(Val, Thr, Ala or Ile); Xaa at res.92=(Arg, Lys, Val, Asp or Glu); Xaa at res.93=(Ala, Gly, Glu or Ser); Xaa at res.95=(Gly or Ala) and Xaa at res.97=(His or Arg).

```
Generic Sequence 6 (Seq. ID No.31)

Cys Xaa Xaa Xaa Xaa Leu Xaa Xaa Xaa Phe
 1               5                   10

Xaa Xaa Xaa Gly Trp Xaa Xaa Trp Xaa
                 15

Xaa Xaa Pro Xaa Xaa Xaa Xaa Ala
 15                  25

Xaa Tyr Cys Xaa Gly Xaa Cys Xaa
         30              35

Xaa Pro Xaa Xaa Xaa Xaa Xaa
                 40

Xaa Xaa Xaa Asn His Ala Xaa Xaa
         45              50

Xaa Xaa Xaa Xaa Xaa Xaa Xaa Xaa
                 55

Xaa Xaa Xaa Xaa Xaa Xaa Xaa Cys
 60                      65

Cys Xaa Pro Xaa Xaa Xaa Xaa Xaa
             70

Xaa Xaa Xaa Leu Xaa Xaa Xaa
 75                  80

Xaa Xaa Xaa Xaa Val Xaa Leu Xaa
             85

Xaa Xaa Xaa Xaa Met Xaa Val Xaa
 90                  95

Xaa Cys Xaa Cys Xaa
         100
``` wherein each Xaa of Generic Sequence 6 (Seq. ID No. 31) is independently selected from a group of one or more specified amino acids as defined by the following: "Res." means "residue" and Xaa at res.2=(Lys, Arg, Ala or Gln); Xaa at res.3=(Lys, Arg or Met); Xaa at res.4=(His, Arg or Gln); Xaa at res.5=(Glu, Ser, His, Gly, Arg, Pro, Thr, or Tyr); Xaa at res.7=(Tyr or Lys); Xaa at res.8=(Val or Ile); Xaa at res.9=(Ser, Asp or Glu); Xaa at res.11=(Arg, Gln, Ser, Lys or Ala); Xaa at res.12=(Asp, Glu, or Lys); Xaa at res.13=(Leu, Val or Ile); Xaa at res.16 =(Gln, Leu, Asp, His, Asn or Ser); Xaa at res.17=(Asp, Arg, Asn or Glu); Xaa at res.19=(Ile or Val); Xaa at res.20=(Ile or Val); Xaa at-res.21=(Ala or Ser); Xaa at res.23=(Glu, Gln, Leu, Lys, Pro or Arg); Xaa at res.24=(Gly or Ser); Xaa at res.25=(Tyr or Phe); Xaa at res.26=(Ala, Ser, Asp, Met, His, Gln, Leu, or Gly); Xaa at res.28=(Tyr, Asn or Phe); Xaa at res.31=(Glu, His, Tyr, Asp, Gln or Ser); Xaa at res.33=Glu, Lys, Asp, Gln or Ala); Xaa at res.35=(Ala, Ser, Pro, Gln or Asn); Xaa at res.36=(Phe, Leu or Tyr); Xaa at res.38=(Leu, Val or Met); Xaa at res.39=(Asn, Asp, Ala, Thr or Pro); Xaa at res.40=(Ser, Asp, Glu, Leu, Ala or Lys); Xaa at res.41=(Tyr, Cys, His, Ser or Ile); Xaa at res.42=(Met, Phe, Gly or Leu); Xaa at res.43=(Asn, Ser or Lys); Xaa at res.44=(Ala, Ser, Gly or Pro); Xaa at res.45=(Thr, Leu or Ser); Xaa at res.49=(Ile, Val or Thr); Xaa at res.50=(Val, Leu or Ile); Xaa at res.51=(Gln or Arg); Xaa at res.52=(Thr, Ala or Ser); Xaa at res.53=(Leu or Ile); Xaa at res.54=(Val or Met); Xaa at res.55=(His, Asn or Arg); Xaa at res.56=(Phe, Leu, Asn, Ser, Ala or Val); Xaa at res.57=(Ile, Met, Asn, Ala, Val or Leu); Xaa at res.58=(Asn, Lys, Ala, Glu, Gly or Phe); Xaa at res.59=(Pro, Ser or Val); Xaa at res.60=(Glu, Asp, Gly, Val or Lys); Xaa at res.61=(Thr, Ala, Val, Lys, Asp, Tyr, Ser, Ala, Pro or His); Xaa at res.62=(Val, Ala or Ile); Xaa at res.63=(Pro or Asp); Xaa at res.64=(Lys, Leu or Glu); Xaa at res.65=(Pro or Ala); Xaa at res.68=(Ala or Val); Xaa at res.70=(Thr, Ala or Glu); Xaa at res.71=(Gln, Lys, Arg or Glu); Xaa at res.72=(Leu, Met or Val); Xaa at res.73=(Asn, Ser, Asp or Gly); Xaa at res.74=(Ala, Pro or Ser); Xaa at res.75=(Ile, Thr, Val or Leu); Xaa at res.76=(Ser, Ala or Pro); Xaa at res.77=(Val, Met or Ile); Xaa at res.79=(Tyr or Phe); Xaa at res.80=(Phe, Tyr, Leu or His); Xaa at res.81=(Asp, Asn or Leu); Xaa at res.82=(Asp, Glu, Asn or Ser); Xaa at res.83=(Ser, Gln, Asn, Tyr or Asp); Xaa at res.84=(Ser, Asn, Asp, Glu or Lys); Xaa at res.85=(Asn, Thr or Lys); Xaa at res.87=(Ile, Val or Asn); Xaa at res.89=(Lys or Arg); Xaa at res.90=(Lys, Asn, Gln, His or Val); Xaa at res.91=(Tyr or His); Xaa at res.92=(Arg, Gln, Glu or Pro); Xaa at res.93=(Asn, Glu or Asp); Xaa at res.95=(Val, Thr, Ala or Ile); Xaa at res.97=(Arg, Lys, Val, Asp or Glu); Xaa at res.98=(Ala, Gly, Glu or Ser); Xaa at res.100=(Gly or Ala); and Xaa at res.102=(His or Arg).

Particularly useful sequences for use as morphogens in this invention include the C-terminal domains, e.g., the C-terminal 96–102 amino acid residues of Vgl, Vgr-1, DPP, OP-1, OP-2, CBMP-2A, CBMP-2B, GDF-1 (see Table II, below, and Seq. ID Nos. 5–14), as well as proteins comprising the C-terminal domains of 60A, BMP3, BMP5 and BMP6 (see Seq. ID Nos. 24–28), all of which include at least the conserved six or seven cysteine skeleton. In addition, biosynthetic constructs designed from the generic sequences, such as COP-1, 3–5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or "similarity", and preferably 80% homology or similarity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes, e.g., those as defined by Dayhoff et al., Atlas of Protein Sequence and Structure; vol. 5, Suppl. 3, pp. 345–362, (M. O. Dayhoff, ed., Nat'l BioMed. Research Fdn., Washington, D.C. 1979). As used herein, potentially useful sequences are aligned with a known morphogen sequence using the method of Needleman et al. ((1970) J.Mol.Biol. 48:443–453) and identities calculated by the Align program (DNAstar, Inc.). "Homology" or "similarity" as used herein includes allowed conservative changes as defined by Dayhoff et al.

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins (e.g., Seq ID Nos. 5, 6, 7, 8, 16, 17, 18, 19, 21 and 23), including the Drosophila 60A protein (e.g., Seq. ID No. 24). Accordingly, in another preferred aspect of the invention, useful morphogens include active proteins comprising species of polypeptide chains having the generic amino acid sequence herein referred to as "OPX" (Seq. ID No. 29), which accommodates the homologies between the various identified species of OP1 and OP2 (Seq. ID Nos. 5, 6, 7, 8, 16, 17, 18, 19, 21 and 23).

The morphogens useful in the methods, composition and devices of this invention include proteins comprising any of the polypeptide chains described above, whether isolated from naturally-occurring sources, or produced by recombinant DNA or other synthetic techniques, and includes allelic and species variants of these proteins, naturally-occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in procaryotic or eucaryotic host cells, and purified, cleaved, refolded, and dimerized to form morphogenically active compositions. Currently preferred host cells include E. coli or mammalian cells, such as CHO, COS or BSC cells. A detailed description of the morphogens useful in the methods, compositions and devices of this invention is disclosed in commonly owed and now abandoned U.S. patent application Ser. No. 752, 764, filed Aug. 30, 1991, and Ser. No. 667,274, filed Mar. 11, 1991 currently pending as Ser. No. 08/404,113, the disclosure of which are incorporated herein by reference.

Thus, in view of this disclosure, skilled genetic engineers can isolate genes from cDNA or genomic libraries of various different species which encode appropriate amino acid sequences, or construct DNAs from oligonucleotides, and then can express them in various types of host cells, including both procaryotes and eucaryotes, to produce large quantities of active proteins capable of protecting tissues and organs from immune cell-mediated tissue destruction, including substantially inhibiting such damage and/or regenerating the damaged tissue in a variety of mammals, including humans.

The foregoing and other objects, features and advantages of the present invention will be made more apparent from the following detailed description of the invention.

DETAILED DESCRIPTION OF THE INVENTION

Figure 1:
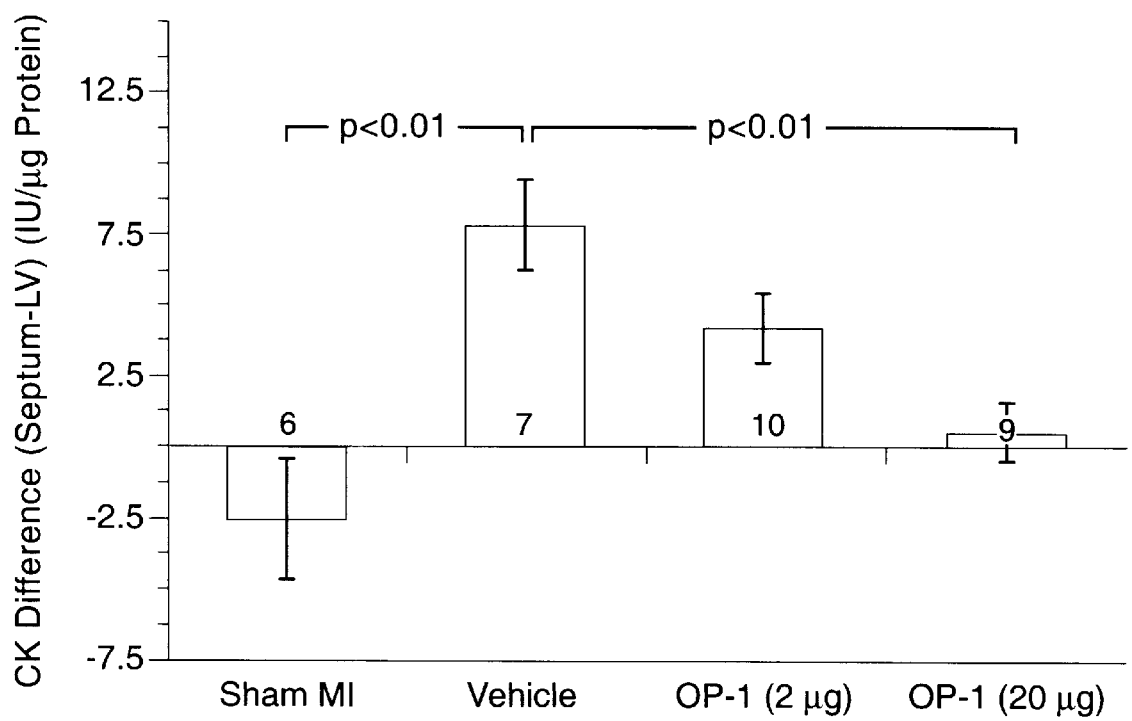
FIG. 1 shows the cardioprotective effects of morphogen (hOP1) in a rat myocardial ischemia-reperfusion model, as evidenced by the smaller loss of myocardial creatine kinase in hoP1-treated rats.

It now has been surprisingly discovered that the morphogens defined herein are effective agents in enhancing the viability of living tissues and organs to be transplanted. Specifically, the morphogens are capable of protecting living tissues and organs to be transplanted from the tissue destructive effects associated with the body's inflammatory response to tissue injury. In one embodiment, the morphogens protect the tissues and organs to be transplanted from the necrotic tissue effects associated with ischemia-reperfusion injury.

When tissue injury occurs, whether caused by bacteria, trauma, chemicals, heat, or any other phenomenon, the body's inflammatory response is stimulated. In response to signals released from the damaged cells (e.g., cytokines), extravascularization of immune effector cells is induced. Under ordinary circumstances these invading immune effector cells kill the infectious agent and/or infected or damaged cells (through the release of killing substances such as superoxides, performs, and other antimicrobial agents stored in granules), remove the dead tissues and organisms (through phagocytosis), release various biological response modifiers that promote rapid healing and covering of the wound (quite often resulting in the formation of fibrotic scar tissue), and then, after the area is successfully healed, exit from the site of the initial insult. Once the site is perceived to be normal, the local release of inflammatory cytokines ceases and the display of adhesion molecules on the vessel endothelium returns to basal levels. In some cases, however, the zeal of these interacting signals and cellular systems, which are designed to capture and contain very rapidly multiplying infectious agents, act to the detriment of the body, killing additional, otherwise healthy, surrounding tissue. This additional-unnecessary tissue death further compromises organ function and sometimes results in death of the individual. In addition, the resulting scar tissue that often forms can interfere with normal tissue function and further inhibit the viability of a transplanted tissue or organ.

Tissue destruction and concomitant loss of tissue function poses significant problems to living tissue and organ transplantation. Once removed from the donor host, living tissue, and particularly harvested organs are at risk for tissue necrosis. The initial injury caused by harvesting the organ may stimulate an immune/inflammatory response in the vascular system within the harvested tissue. In addition, any tissue damage that occurs to the harvested organ prior to transplantation likely will stimulate an inflammatory response in the recipient host upon transplantation. This response can induce additional tissue destruction and/or fibrogenesis, or scar tissue formation, both of which can inhibit tissue activity and viability.

The vascular endothelium constitutes the first barrier between circulating immune effector cells and extravascular tissues. Extravasation of these circulating cells requires that they bind to the vascular endothelial cells, cross the basement membrane, and enter insulted tissues, e.g., by phagocytosis or protease-mediated extracellular matrix degradation. Without being limited to a particular theory, it is believed that the morphogens of this invention may modulate the inflammatory response in part by modulating the attachment of immune effector cells to the luminal side of the endothelium of blood vessels at or near sites of tissue damage and/or inflammatory lesions. Because the method reduces or prevents the attachment of immune effector cells at these sites, it also prevents the subsequent release of tissue destructive agents by these same immune effector cells at sites of tissue damage and/or inflammatory lesions. Because attachment of immune effector cells to the endothelium must precede their extravascularization, the method also prevents the initial or continued entry of these cells into extravascular sites of tissue destruction or ongoing inflammatory lesions. Therefore, the invention not only relates to a method to reduce or prevent the immune cell-mediated cellular destruction at extravascular sites of recent tissue destruction, but also relates to a method to prevent or reduce the continued entry of immune effector cells into extravascular sites of ongoing inflammatory cascades. As will be appreciated by those skilled in the art, the morphogens of this invention also may be contemplated in mechanisms for disrupting the functional interaction of immune effector cells with endothelium where the adhesion molecules are induced by means other than in response to tissue injury.

The morphogens, when provided to the tissue or organ to be transplanted, can protect these tissues and organs from immune cell-mediated tissue damage. The morphogens preferably are provided to the tissue or organ prior to stimulation of tissue destruction. However, the morphogens also can alleviate tissue damage to organs and living tissue to be transplanted, by stimulating regeneration of the damaged tissue and/or inhibiting additional damage to the tissue.

One particular source of tissue injury to which transplants are particularly at risk, is induced by cell exposure to toxic oxygen concentrations, such as the tissue damage induced following ischemic-reperfusion injury (oxygen deprivation), and following hyperoxia injury (lethally high oxygen concentrations). Accordingly, the present invention provides methods and compositions for alleviating the tissue damage associated with ischemic-reperfusion injury or hyperoxia-induced injury that include providing to the living tissue or organ a therapeutically effective concentration of a morphogen prior to, during, or after damage to the tissue.

In addition, the morphogens described herein, in contrast to fibrogenic growth factors such as TGF-β, stimulate tissue morphogenesis and do not stimulate fibrosis or scar tissue formation (see Example 7, below.) Accordingly, in addition to inhibiting the tissue destructive effects associated with the inflammatory response, the morphogens further enhance the viability of damaged tissue and/or organs by stimulating the regeneration of the damaged tissue and preventing fibrogenesis.

Provided below are detailed descriptions of suitable morphogens useful in the methods and compositions of this invention, as well as methods for their administration and application, and numerous, nonlimiting examples which 1) illustrate the suitability of the morphogens and morphogen-stimulating agents described herein as therapeutic agents for protecting tissue from the tissue destructive effects associated with the body's inflammatory response; and 2) provide assays with which to test candidate morphogens and morphogen-stimulating agents for their efficacy.

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogens useful in the method of this invention first were identified, as well as a description on how to make, use and test them for morphogenic activity are disclosed in commonly owned and now abandoned U.S. Ser. No. 667,274, filed Mar. 11, 1991 and U.S. Ser. No. 752,764, filed Aug. 30, 1991 currently pending as U.S. Ser. No. 08/404,113, the disclosures of which are hereinabove incorporated by reference.

A candidate morphogen or morphogen composition can be evaluated for in vivo morphogenic utility generally according to the procedures set forth in U.S. Ser. No. 07/752,764. The proteins and compositions may be injected or surgically implanted in a mammal, following any of a number of procedures well known in the art. For example, surgical implant bioassays may be performed essentially following the procedure of Sampath et al. (1983) PNAS 80:6591–6595.

Histological sectioning and staining is preferred to determine the extent of morphogenesis in vivo, particularly in tissue repair procedures. Excised implants are fixed in Bouins Solution, embedded in paraffin, and cut into 6–8 $\mu$m sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;

(2) mesenchymal cell migration and proliferation on days two and three;

(3) chondrocyte appearance on days five and six;

(4) cartilage matrix formation on day seven;

(5) cartilage calcification on day eight;

(6) vascular invasion, appearance of osteoblasts, and formation of new bone on days nine and ten;

(7) appearance of osteoblastic and bone remodeling and dissolution of the implanted matrix on days twelve to eighteen; and (8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided.

The morphogen to be assayed according to the above-described exemplary procedures can be purified from naturally-sourced material, or can be recombinantly produced from procaryotic or eucaryotic host cells, into which genetic material encoding a morphogen, e.g., genetic material bearing one of the nucleic acid sequences disclosed herein, has been introduced. Alternatively, the above-described exemplary procedures can be used to determine whether a novel protein suspected of being a morphogen indeed has morphogenic activity.

Particularly useful proteins include those which comprise the naturally derived sequences disclosed in Table II. Other useful sequences include biosynthetic constructs such as those disclosed in U.S. Pat. No. 5,011,691, the disclosure of which is incorporated herein by reference (e.g., COP-1, COP-3, COP-4, COP-5, COP-7, and COP-16).

Accordingly, the morphogens useful in the methods and compositions of this invention also may be described by morphogenically active proteins having amino acid sequences sharing 70% or, preferably, 80% homology (similarity) with any of the sequences described above, where "homology" is as defined herein above.

The morphogens useful in the method of this invention also can be described by any of the 6 generic sequences described herein (Generic Sequences 1, 2, 3, 4, 5 and 6, Seq. ID Nos. 1, 2, 3, 4, 30 and 31). Generic sequences 1 and 2 (Seq. ID Nos. 1 and 2) also may include, at their N-terminus, the sequence

```
Cys Xaa Xaa Xaa Xaa (Seq. ID No. 15)
 1               5
```

Table II, set forth below, compares the amino acid sequences of the active regions of native proteins that have been identified as morphogens, including human OP-1 (hOP-1, Seq. ID Nos. 5 and 16–17), mouse OP-1 (mOP-1, Seq. ID Nos. 6 and 18–19), human and mouse OP-2 (Seq. ID Nos. 7, 8, and 20–23), CBMP2A (Seq. ID No. 9), CBMP2B (Seq. ID No. 10), BMP3 (Seq. ID No. 26), DPP (from Drosophila, Seq. ID No. 11), Vgl, (from Xenopus, Seq. ID No. 12), Vgr-1 (from mouse, Seq. ID No. 13), GDF-1 (from mouse, Seq. ID Nos. 14, 32 and 33), 60A protein (from Drosophila, Seq. ID Nos. 24 and 25), BMP5 (Seq. ID No. 27) and BMP6 (Seq. ID No. 28). The sequences are aligned essentially following the method of Needleman et al. (1970) *J. Mol. Biol.,* 48:443–453, calculated using the Align Program (DNAstar, Inc.) In the table, three dots indicates that the amino acid in that position is the same as the amino acid in hOP-1. Three dashes indicates that no amino acid is present in that position, and are included for purposes of illustrating homologies. For example, amino acid residue 60 of CBMP-2A and CBMP-2B is "missing". Of course, both these amino acid sequences in this region comprise Asn-Ser (residues 58, 59), pith CBMP-2A then comprising Lys and Ile, whereas CBMP-2B comprises Ser and Ile.

TABLE II

| | Seq ID No: | 1 | | | | 5 | | | | | 10 | | | | | 15 | |
|---|---|---|---|---|---|---|---|---|---|---|---|---|---|---|---|---|---|
| hOP-1 | 5 | Cys | Lys | Lys | His | Glu | Leu | Tyr | Val | Ser | Phe | Arg | Asp | Leu | Gly | Trp | Gln |
| mOP-1 | 6 | — | — | — | — | — | — | — | — | — | — | — | — | — | — | — | — |
| hOP-2 | 7 | — | Arg | Arg | — | — | — | — | — | — | — | Gln | — | — | — | — | Leu |
| mOP-2 | 8 | — | Arg | Arg | — | — | — | — | — | Ser | — | — | — | — | — | — | Leu |
| DPP | 11 | — | Arg | Arg | — | Ser | — | — | — | Asp | — | Ser | — | Val | — | — | Asp |
| Vgl | 12 | — | — | Lys | Arg | His | — | — | — | Glu | — | Lys | — | Val | — | — | — |
| Vgr-1 | 13 | — | — | — | — | Gly | — | — | — | — | — | Gln | — | Val | — | — | — |
| CBMP-2A | 9 | — | — | Arg | — | Pro | — | — | — | Asp | — | Ser | — | Val | — | — | Asn |
| CBMP-2B | 10 | — | Arg | Arg | — | Ser | — | — | — | Asp | — | Ser | — | Val | — | — | Asn |
| BMP3 | 26 | — | Ala | Arg | Arg | Tyr | — | Lys | — | Asp | — | Ala | — | Ile | — | — | Ser |
| GDF-1 | 14 | — | Arg | Ala | Arg | Arg | — | — | — | — | — | — | Glu | Val | — | — | His |
| 60A | 25 | — | Gln | Met | Glu | Thr | — | — | — | Asp | — | Lys | — | — | — | — | His |
| BMP5 | 27 | — | — | — | — | — | — | — | — | — | — | — | — | — | — | — | — |
| BMP6 | 28 | — | Arg | — | — | — | — | — | — | — | — | GJn | — | — | — | — | — |

| | Seq ID No: | | | | | 20 | | | | | 25 | | | | | 30 | |
|---|---|---|---|---|---|---|---|---|---|---|---|---|---|---|---|---|---|
| hOP-1 | 5 | Asp | Trp | Ile | Ile | Ala | Pro | Glu | Gly | Tyr | Ala | Ala | Tyr | Tyr | Cys | Glu | Gly |
| mOP-1 | 6 | — | — | — | — | — | — | — | — | — | — | — | — | — | — | — | — |
| hOP-2 | 7 | — | — | Val | — | — | — | Gln | — | — | Ser | — | — | — | — | — | — |
| mOP-2 | 8 | — | — | Val | — | — | — | Gln | — | — | Ser | — | — | — | — | — | — |
| DPP | 11 | — | — | — | Val | — | — | Leu | — | — | Asp | — | — | — | — | His | — |
| Vgl | 12 | Asn | — | Val | — | — | — | Gln | — | — | Met | — | Asn | — | — | Tyr | — |
| Vgr-1 | 13 | — | — | — | — | — | — | Lys | — | — | — | — | Asn | — | — | Asp | — |
| CBMP-2A | 9 | — | — | — | Val | — | — | Pro | — | — | His | — | Phe | — | — | His | — |
| CBMP-2B | 10 | — | — | — | Val | — | — | Pro | — | — | — | Gln | — | — | Phe | His | — |
| BMP3 | 26 | Glu | — | — | — | Ser | — | Lys | Ser | Phe | Asp | — | — | — | — | Ser | — |
| GDF-1 | 14 | Arg | — | Val | — | — | — | Arg | — | Phe | Leu | — | Asn | — | — | Gln | — |
| 60A | 25 | — | — | — | — | — | — | — | — | — | Gly | — | Phe | — | — | Ser | — |
| BMP5 | 27 | — | — | — | — | — | — | — | — | — | — | — | Phe | — | — | Asp | — |
| BMP6 | 28 | — | — | — | — | — | — | Lys | — | — | — | — | Asn | — | — | Asp | — |

| | Seq ID No: | | | | | 35 | | | | | 40 | | | | | 45 | |
|---|---|---|---|---|---|---|---|---|---|---|---|---|---|---|---|---|---|
| hOP-1 | 5 | Glu | Cys | Ala | Phe | Pro | Leu | Asn | Ser | Tyr | Met | Asn | Ala | Thr | Asn | His | Ala |
| mOP-1 | 6 | — | — | — | — | — | — | — | — | — | — | — | — | — | — | — | — |
| hOP-2 | 7 | — | — | Ser | — | — | — | Asp | — | Cys | — | — | — | — | — | — | — |
| mOP-2 | 8 | — | — | — | — | — | — | Asp | — | Cys | — | — | — | — | — | — | — |
| DPP | 11 | Lys | — | Pro | — | — | — | Ala | Asp | His | Phe | — | Ser | — | — | — | — |
| Vgl | 12 | — | — | Pro | Tyr | — | — | Thr | Glu | Ile | Leu | — | Gly | Ser | — | — | — |
| Vgr-1 | 13 | — | — | Ser | — | — | — | — | Ala | His | — | — | — | — | — | — | — |
| CBMP-2A | 9 | Glu | — | Pro | — | — | — | Ala | Asp | His | Leu | — | Ser | — | — | — | — |
| CBMP-2B | 10 | Asp | — | Pro | — | — | — | Ala | Asp | His | Leu | — | Ser | — | — | — | — |
| BMP3 | 26 | Ala | — | Gln | — | — | Met | Pro | Lys | Ser | Leu | Lys | Pro | Ser | — | — | — |
| GDF-1 | 14 | Gln | — | — | Leu | — | Val | Ala | Leu | Ser | Gly | Ser** | — | Leu | — | — | — |
| 60A | 25 | — | — | Asn | — | — | — | — | Ala | His | — | — | — | — | — | — | — |
| BMP5 | 27 | — | — | Ser | — | — | — | — | Ala | His | Met | — | — | — | — | — | — |
| BMP6 | 28 | — | — | Ser | — | — | — | — | Ala | His | Met | — | — | — | — | — | — |

TABLE II-continued

| Seq ID No: | | | | | | | | | | | | | | | | | | |
|---|---|---|---|---|---|---|---|---|---|---|---|---|---|---|---|---|---|---|
| hOP-1 | 5 | Ile | Val | Gln | Thr | Leu | Val | His | Phe | Ile | Asn | Pro | Glu | Thr | Val | Pro | Lys |
| mOP-1 | 6 | — | — | — | — | — | — | — | — | — | — | — | Asp | — | — | — | — |
| hOP-2 | 7 | — | Leu | — | Ser | — | — | His | Leu | Met | Lys | — | Asn | Ala | — | — | — |
| mOP-2 | 8 | — | Leu | — | Ser | — | — | His | Leu | Met | Lys | — | Asp | Val | — | — | — |
| DPP | 11 | Val | — | — | — | — | — | Asn | Asn | Asn | — | — | Gly | Lys | — | — | — |
| Vgl | 12 | — | Leu | — | — | — | — | — | Ser | — | Glu | — | — | Asp | Ile | — | Leu |
| Vgr-1 | 13 | — | — | — | — | — | — | — | Val | Met | — | — | — | Tyr | — | — | — |
| CBMP-2A | 9 | — | — | — | — | — | — | Asn | Ser | Val | — | Ser | — | Lys | Ile | — | — |
| CBMP-2B | 10 | — | — | — | — | — | — | Asn | Ser | Val | — | Ser | — | Ser | Ile | — | — |
| BMP3 | 26 | Thr | Ile | — | Ser | Ile | — | Arg | Ala** | Gly | Val | Val | Pro | Gly | Ile | — | Glu |
| GDF-1 | 14 | Val | Leu | Arg | Ala | — | Met | — | Ala | Ala | Ala | — | Gly | Ala | Ala | Asp | Leu |
| 60A | 25 | — | — | — | — | — | — | — | Leu | Leu | Glu | — | Lys | Lys | — | — | — |
| BMP5 | 27 | — | — | — | — | — | — | — | Leu | Met | Phe | — | Asp | His | — | — | — |
| BMP6 | 28 | — | — | — | — | — | — | — | Leu | Met | — | — | — | Tyr | — | — | — |
| | | | | 50 | | | | | 55 | | | | | 60 | | | | |

| | | | | | | | | | | | | | | | | | | |
|---|---|---|---|---|---|---|---|---|---|---|---|---|---|---|---|---|---|---|
| hOP-1 | 5 | Pro | Cys | Cys | Ala | Pro | Thr | Gln | Leu | Asn | Ala | Ile | Ser | Val | Leu | Tyr | Phe |
| mOP-1 | 6 | — | — | — | — | — | — | — | — | — | — | — | — | — | — | — | — |
| hOP-2 | 7 | Ala | — | — | — | — | — | Lys | — | Ser | — | Thr | — | — | — | — | Tyr |
| mOP-2 | 8 | Ala | — | — | — | — | — | Lys | — | Ser | — | Thr | — | — | — | — | Tyr |
| DPP | 11 | Ala | — | — | Val | — | — | — | — | Asp | Ser | Val | Ala | Met | — | — | Leu |
| Vgl | 12 | — | — | — | Val | — | — | Lys | Met | Ser | Pro | — | — | Met | — | Phe | Tyr |
| Vgr-1 | 13 | — | — | — | — | — | — | Lys | Val | — | — | — | — | — | — | — | — |
| CBMP-2A | 9 | Ala | — | — | Val | — | — | Glu | — | Ser | — | — | — | Met | — | — | Leu |
| CBMP-2B | 10 | Ala | — | — | Val | — | — | Glu | — | Ser | — | — | — | Met | — | — | Leu |
| BMP3 | 26 | — | — | — | Val | — | Glu | Lys | Met | Ser | Ser | Leu | — | Ile | — | Phe | Tyr |
| GDF-1 | 14 | — | — | — | Val | — | Ala | Arg | — | Ser | Pro | — | — | — | — | Phe | — |
| 60A | 25 | — | — | — | — | — | — | Arg | — | Gly | — | Leu | Pro | — | — | — | His |
| BMP5 | 27 | — | — | — | — | — | — | Lys | — | — | — | — | — | — | — | — | — |
| BMP6 | 28 | — | — | — | — | — | — | Lys | — | — | — | — | — | — | — | — | — |
| | | | 65 | | | | | 70 | | | | | 75 | | | | | 80 |

| | | | | | | | | | | | | | | | | | | |
|---|---|---|---|---|---|---|---|---|---|---|---|---|---|---|---|---|---|---|
| hOP-1 | 5 | Asp | Asp | Ser | Ser | Asn | Val | Ile | Leu | Lys | Lys | Tyr | Arg | Asn | Met | Val | Val |
| mOP-1 | 6 | — | — | — | — | — | — | — | — | — | — | — | — | — | — | — | — |
| hOP-2 | 7 | — | Ser | — | Asn | — | — | — | — | Arg | — | His | — | — | — | — | — |
| mOP-2 | 8 | — | Ser | — | Asn | — | — | — | — | Arg | — | His | — | — | — | — | — |
| DPP | 11 | Asn | — | Gln | — | Thr | — | Val | — | — | Asn | — | Gln | Glu | — | Thr | — |
| Vgl | 12 | — | Asn | Asn | Asp | — | — | Val | — | Arg | His | — | Glu | — | — | Ala | — |
| Vrg-1 | 13 | — | — | Asn | — | — | — | — | — | — | — | — | — | — | — | — | — |
| CBMP-2A | 9 | — | Glu | Asn | Glu | Lys | — | Val | — | — | Asn | — | Gln | Asp | — | — | — |
| CBMP-2B | 10 | — | Glu | Tyr | Asp | Lys | — | Val | — | — | Asn | — | Gln | Glu | — | — | — |
| BMP3 | 26 | — | Glu | Asn | Lys | — | — | Val | — | — | Val | — | Pro | — | — | Thr | — |
| GDF-1 | 14 | — | Asn | — | Asp | — | — | Val | — | Arg | Gln | — | Glu | Asp | — | — | — |
| 60A | 25 | Leu | Asn | Asp | Glu | — | — | Asn | — | — | — | — | — | — | — | Ile | — |
| BMP5 | 27 | — | — | — | — | — | — | — | — | — | — | — | — | — | — | — | — |
| BMP6 | 28 | — | — | Asn | — | — | — | — | — | — | — | — | — | Trp | — | — | — |
| | | | | | 85 | | | | | 90 | | | | | 95 | | | |

| | | | | | | | |
|---|---|---|---|---|---|---|---|
| hOP-1 | 5 | Arg | Ala | Cys | Gly | Cys | His |
| mOP-1 | 6 | — | — | — | — | — | — |
| hOP-2 | 7 | Lys | — | — | — | — | — |
| mOP-2 | 8 | Lys | — | — | — | — | — |
| DPP | 11 | Val | Gly | — | — | — | Arg |
| Vgl | 12 | Asp | Glu | — | — | — | Arg |
| Vgr-1 | 13 | — | — | — | — | — | — |
| CBMP-2A | 9 | Glu | Gly | — | — | — | Arg |
| CBMP-2B | 10 | Glu | Gly | — | — | — | Arg |
| BMP3 | 26 | Glu | Ser | — | Ala | — | Arg |
| GDF-1 | 14 | Asp | Glu | — | — | — | Arg |
| 60A | 25 | Lys | Ser | — | — | — | — |
| BMP5 | 27 | — | Ser | — | — | — | — |
| BMP6 | 28 | — | — | — | — | — | — |
| — | | — | — | — | 100 | — | 102 |

**Between residues 56 and 57 of BMP3 (Seq. ID No. 26) is a Val residue; between residues 43 and 44 of GDF-1 (Seq. ID No. 14) lies the amino acid sequence (Gly—Gly—Pro—Pro.

As is apparent from the foregoing amino acid sequence comparisons, significant amino acid changes can be made within the generic sequences while retaining the morphogenic activity. For example, while the GDF-1 protein sequence depicted in Table II shares only about 50% amino acid identity with the hOP1 sequence described therein, the GDF-1 sequence shares greater than 70% amino acid sequence homology (or "similarity") with the hOP1 sequence, where "homology" or "similarity" includes allowed conservative amino acid changes within the sequence as defined by Dayhoff, et al., *Atlas of Protein Sequence and Structure* vol.5, supp.3, pp.345–362, (M. O. Dayhoff, ed., Nat'l BioMed. Res. Fd'n, Washington D.C. 1979.)

The currently most preferred protein sequences useful as morphogens in this invention include those having greater than 60% identity, preferably greater than 65% identity, with the amino acid sequence defining the conserved six cysteine skeleton of hOP1 (e.g., residues 43–139 of Seq. ID No. 5). These most preferred sequences include both allelic and species variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX" (Seq. ID No. 29), which defines the seven cysteine skeleton and accommodates the identities between the various identified mouse and human OP1 and OP2 proteins. OPX is presented in Seq. ID No. 29. As described therein, each Xaa at a given position independently is selected from the residues occurring at the corresponding position in the C-terminal sequence of mouse or human OP1 or OP2 (see Seq. ID Nos. 5–8 and/or Seq. ID Nos. 16–23).

II. Formulations and Methods for Administering Therapeutic Agents

Where the morphogen or morphogen-stimulating agent comprises part of a tissue or organ preservation solution, any commercially available preservation solution may be used to advantage. For example, useful solutions known in the art include Collins solution, Wisconsin solution, Belzer solution, Eurocollins solution and lactated Ringer's solution. Generally, an organ preservation solution usually possesses one or more of the following properties: (a) an osmotic pressure substantially equal to that of the inside of a mammalian cell,(solutions typically are hyperosmolar and have K+ and/or Mg++ ions present in an amount sufficient to produce an osmotic pressure slightly higher than the inside of a mammalian cell); (b) the solution typically is capable of maintaining substantially normal ATP levels in the cells; and (c) the solution usually allows optimum maintenance of glucose metabolism in the cells. organ preservation solutions also may contain anticoagulants, energy sources such as glucose, fructose and other sugars, metabolites, heavy metal chelators, glycerol and other materials of high viscosity to enhance survival at low temperatures, free oxygen radical inhibiting agents and a pH indicator. A detailed description of preservation solutions and useful components may be found, for example, in U.S. Pat. No. 5,002,965, the disclosure of which is incorporated herein by reference.

Where the morphogen or morphogen-stimulating agent is to be provided to an individual, e.g., the donor prior to harvest, or the recipient prior to or concomitant with transplantation, the therapeutic agent may be provided by any suitable means, preferably directly (e.g., locally, as by injection to the tissue or organ locus) or systemically (e.g., parenterally or orally). Where the morphogen is to be provided directly by injection, or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (9.85% NaCl, 0.15M), pH 7–7.4. The aqueous solution containing the morphogen can be made, for example, by dissolving the protein in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, association of the mature dimer with the pro domain of the morphogen increases solubility of the protein significantly. In fact, the endogenous protein is thought to be transported in this form. Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the morphogen at the desired locus. Biocompatible, preferably bioresorbable, polymers, including, for example, hyaluronic acid, collagen, tricalcium phosphate, polybutyrate, lactide and glycolide polymers and lactide/glycolide copolymers, may be useful excipients to control the release of the morphogen in vivo. Other potentially useful parenteral delivery systems for these morphogens include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

Alternatively, the morphogens described herein may be administered orally to a donor or recipient host. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590.) In addition, at least one morphogen, OP-1, has been identified in mammary gland extract, colostrum and 57-day milk. Moreover, the OP-1 purified from mammary gland extract is morphogenically active. Specifically, this protein induces endochondral bone formation in mammals when implanted subcutaneously in association with a suitable matrix material, using a standard in vivo bone assay, such as is disclosed in U.S. Pat. No. 4,968,590. Moreover, the morphogen also is detected in the bloodstream. Finally, soluble form morphogen, e.g., mature morphogen associated with the pro domain, is morphogenically active. These findings indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also may be associated with molecules capable of enhancing their solubility in vitro or in vivo.

The compounds provided herein also may be associated with molecules capable of targeting the morphogen or morphogen-stimulating agent to target tissue or organ to be transplanted. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513.

As described above, the morphogens provided herein share significant sequence homology in the C-terminal active domains. By contrast, the sequences typically diverge significantly in the sequences which define the pro domain. Accordingly, the pro domain is thought to be morphogen-specific. As described above, it is also known that the various morphogens identified to date are differentially expressed in the different tissues. Accordingly, without being limited to any given theory, it is likely that, under natural conditions in the body, selected morphogens typically act on a given tissue. Accordingly, part or all of the pro domains which have been identified associated with the active form of the morphogen in solution, may serve as targeting molecules for the morphogens described herein. For example, the pro domains may interact specifically with one or more molecules at the target tissue to direct the morphogen associated with the pro domain to that tissue. Accordingly, another useful targeting molecule for targeting morphogen to a tissue of interest may be part or all of a morphogen pro domain.

Finally, the morphogens or morphogen-stimulating agents provided herein may be administered to a donor or recipient alone or in combination with other molecules known to be beneficial in the compositions and methods described herein, including, but not limited to, anticoagulants, free oxygen radical inhibiting agents, salicylic acid, vitamin D, and other antiinflammatory agents.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated in therapeutically effective amounts, e.g., amounts which provide appropriate concentrations for a time sufficient to enhance the viability of a tissue or organ to be transplanted, including protecting the tissue or organ to be transplanted from the tissue destructive effects associated with the inflammatory response, and/or alleviating any tissue damage to the transplants, including protecting them from the tissue destructive effects associated with ischemia-reperfusion injury.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. Where the morphogen or morphogen-stimulating agent is part of a preservation solution, the dosage likely will depend for example, on the size of the tissue or organ to be transplanted, the overall health status of the organ or tissue itself, the length of time between harvest and transplantation (e.g., the duration in storage), the frequency with which the preservation solution is changed, and the type of storage anticipated, e.g., low temperature. In general terms, preferred ranges include a concentration range between about 0.1 ng to 100 μg/kg per tissue or organ weight per day.

Where the therapeutic agent is to be administered to a donor or recipient, the preferred dosage of drug to be administered also is likely to depend on such variables as the type and extent of progression of the disease, the overall health status of the particular patient, the relative biological efficacy of the compound selected, the formulation of the compound excipients, and its route of administration. In general terms, the compounds of this invention may be provided in an aqueous physiological buffer solution containing about 0.001% to 10% w/v compound for parenteral administration. Typical dose ranges are from about 10 ng/kg to about 1 g/kg of body weight per day; a preferred dose range is from about 0.1 μg/kg to 100 mg/kg of body weight per day. Optimally, the morphogen dosage given is between 0.1–100 μg of protein per kilogram weight of the patient.

No obvious morphogen induced pathological lesions are induced when mature morphogen (e.g., OP-1, 20 μg) is administered daily to normal growing rats for 21 consecutive days. Moreover, 10 μg systemic injections of morphogen (e.g., OP-1) injected daily for 10 days into normal newborn mice does not produce any gross abnormalities.

Alternatively, an effective amount of an agent capable of stimulating endogenous morphogen levels may be administered by any of the routes described above. For example, an agent capable of stimulating morphogen production and/or secretion from tissue or organ cells of interest may be provided to a mammal, e.g., by direct administration of the agent to the tissue to be transplanted. A method for identifying and testing agents capable of modulating the levels of endogenous morphogens in a given tissue is described generally herein in Example 8, and in detail in copending U.S. Ser. No. 752,859, filed Aug. 30, 1991, the disclosure of which is incorporated herein by reference. Briefly, candidate compounds can be identified and tested by incubating the compound in vitro with a test tissue or cells thereof, for a time sufficient to allow the compound to affect the production, i.e., the expression and/or secretion, of a morphogen produced by the cells of that tissue.

For purposes of the present invention, the above-described morphogens effective in alleviating ischemic-reperfusion injury are administered prior to or during the restoration of oxygen (e.g., restoration of blood flow, reperfusion.) Where treatment is to follow an existing injury, the morphogen preferably is administered as an intravenous infusion provided acutely after the hypoxic or ischemic condition occurs. Where ischemia or hypoxia is deliberately induced as part of, for example, a surgical procedure where circulation to an organ or organ system is unavoidably or deliberately reduced or interrupted, e.g., transiently, as in a tissue or organ transplantation or grafting procedure, the morphogen preferably is provided just prior to, or concomitant with, reduction of oxygen to the tissue. Preferably, the morphogen is administered prophylactically in a surgical setting. Optimally, the morphogen dosage given is in the range of about 0.1–100 μg of protein per kilogram weight of the patient.

III. EXAMPLES

Example 1

Identification of Morphogen-Expressing Tissue

Determining the tissue distribution of morphogens may be used to identify different morphogens expressed in a given tissue, as well as to identify new, related morphogens. Tissue distribution also may be used to identify useful morphogen-producing tissue for use in screening and identifying candidate morphogen-stimulating agents. The morphogens (or their mRNA transcripts) readily are identified in different tissues using standard methodologies and minor modifications thereof in tissues where expression may be low. For example, protein distribution may be determined using standard Western blot analysis or immunofluorescent techniques, and antibodies specific to the morphogen or morphogens of interest. Similarly, the distribution of morphogen transcripts may be determined using standard Northern hybridization protocols and transcript-specific probes.

Any probe capable of hybridizing specifically to a transcript, and distinguishing the transcript of interest from other, related transcripts may be used. Because the morphogens described herein share such high sequence homology in their active, C-terminal domains, the tissue distribution of a specific morphogen transcript may best be determined using a probe specific for the pro region of the immature protein and/or the N-terminal region of the mature protein. Another useful sequence is the 3' non-coding region flanking and immediately following the stop codon. These portions of the sequence vary substantially among the morphogens of this invention, and accordingly, are specific for each protein. For example, a particularly useful Vgr-1-specific probe sequence is the PvuII-SacI fragment, a 265 bp fragment encoding both a portion of the untranslated pro region and the N-terminus of the mature sequence (see Lyons et al. (1989) *PNAS* 86:4554–4558 for a description of the cDNA sequence). Similarly, particularly useful mOP-1-specific probe sequences are the BstX1-BglI fragment, a 0.68 Kb sequence that covers approximately two-thirds of the mOP-1 pro region; a StuI-StuI fragment, a 0.2 Kb sequence immediately upstream of the 7-cysteine domain; and the EarI-PstI fragment, an 0.3 Kb fragment containing a portion of the 3'untranslated sequence (See Seq. ID No. 18, where the pro region is defined essentially by residues 30–291.) Similar approaches may be used, for example, with hOP-1 (Seq. ID No. 16) or human or mouse OP-2 (Seq. ID Nos. 20 and 22.)

Using these morphogen-specific probes, which may be synthetically engineered or obtained from cloned sequences, morphogen transcripts can be identified in mammalian tissue, using standard methodologies well known to those having ordinary skill in the art. Briefly, total RNA is prepared from various adult murine tissues (e.g., liver, kidney, testis, heart, brain, thymus and stomach) by a standard methodology such as by the method of Chomczyaski et al. ((1987) *Anal. Biochem* 162:156–159) and described below. Poly (A)+ RNA is prepared by using oligo (dT)-cellulose chromatography (e.g., Type 7, from Pharmacia LKB Biotechnology, Inc.). Poly (A)+ RNA (generally 15 μg) from each tissue is fractionated on a 1% agarose/formaldehyde gel and transferred onto a Nytran membrane (Schleicher & Schuell). Following the transfer, the membrane is baked at 80° C. and the RNA is cross-linked under UV light (generally 30 seconds at 1 mW/cm$^2$). Prior to hybridization, the appropriate probe is denatured by heating. The hybridization is carried out in a lucite cylinder rotating in a roller bottle apparatus at approximately 1 rev/min for approximately 15 hours at 37° C. using a hybridization mix of 40% formamide, 5× Denhardts, 5× SSPE, and 0.1% SDS. Following hybridization, the non-specific counts are washed off the filters in 0.1× SSPE, 0.1% SDS at 50° C.

Examples demonstrating the tissue distribution of various morphogens, including Vgr-1, OP-1, BMP2, BMP3, BMP4, BMP5, GDF-1, and OP-2 in developing and adult tissue are disclosed in co-pending U.S. Ser. No. 752,764, and in Ozkaynak, et al., (1991) *Biochem. Bicphys. Res. Commn.* 179:116–123, and Ozkaynak, et al. (1992) (JBC, in press), the disclosures of which are incorporated herein by reference. Using the general probing methodology described herein, northern blot hybridizations using probes specific for these morphogens to probe brain, spleen, lung, heart, liver and kidney tissue indicate that kidney-related tissue appears to be the primary expression source for OP-1, with brain, heart and lung tissues being secondary sources. OP-1 mRNA also was identified in salivary glands, specifically rat parotid glands, using this probing methodology. Lung tissue appears to be the primary tissue expression source for Vgr-1, BMP5, BMP4 and BMP3. Lower levels of Vgr-1 also are seen in kidney and heart tissue, while the liver appears to be a secondary expression source for BMP5, and the spleen appears to be a secondary expression source for BMP4. GDF-1 appears to be expressed primarily in brain tissue. To date, OP-2 appears to be expressed primarily in early embryonic tissue. Specifically, northern blots of murine embryos and 6-day post-natal animals shows abundant OP2 expression in 8-day embryos. Expression is reduced significantly in 17-day embryos and is not detected in post-natal animals.

Example 2

Active Morphogens in Body Fluids

OP-1 expression has been identified in saliva (specifically, the rat parotid gland, see Example 1), human blood serum, and various milk forms, including mammary gland extract, colostrum, and 57-day bovine milk. Moreover, and as described in U.S. Ser. No. 923,780 (commonly owned and now abandoned), currently pending as Ser. No. 08/432,883, the disclosure of which is incorporated herein by reference, the body fluid-extracted protein is morphogenically active. The discovery that the morphogen naturally is present in milk and saliva, together with the known observation that mature, active OP-1 is acid-stable and protease-resistant, indicate that oral administration is a useful route for therapeutic administration of morphogen to a mammal. Oral administration typically is the preferred mode of delivery for extended or prophylactic therapies. In addition, the identification of morphogen in all milk forms, including colostrum, suggests that the protein may play a significant role in tissue development, including skeletal development, of juveniles.

2.1 Morphogen Detection in Milk

OP-1 was partially purified from rat mammary gland extract and bovine colostrum and 57 day milk by passing these fluids over a series of chromatography columns: (e.g., cation-exchange, affinity and reverse phase). At each step the eluant was collected in fractions and these were tested for the presence of OP-1 by standard immunoblot. Immunoreactive fractions then were combined and purified further. The final, partially purified product then was examined for the presence of OP-1 by Western blot analysis using OP-1-specific antisera, and tested for in vivo and in vitro activity.

OP-1 purified from the different milk sources were characterized by Western blotting using antibodies raised against OP-1 and BMP2. Antibodies were prepared using standard immunology protocols well known in the art, and as described generally in Example 12, below, using full-length *E. coli*-produced OP-1 and BMP2 as the immunogens. In all cases, the purified OP-1 reacted only with the anti-OP-1 antibody, and not with anti-BMP2 antibody.

The morphogenic activity of OP-1 purified from mammary gland extract was evaluated in vivo essentially following the rat model assay described in U.S. Pat. No. 4,968,590, hereby incorporated by reference. Briefly, a sample was prepared from each OP-1 immunoreactive fraction of the mammary gland extract-derived OP-1 final product by lyophilizing a portion (33%) of the fraction and resuspending the protein in 220 µl of 50% acetonitrile/0.1% TFA. After vortexing, 25 mg of collagen matrix was added. The samples were lyophilized overnight, and implanted in Long Evans rats (Charles River Laboratories, Wilmington, Mass., 28–35 days old). Each fraction was implanted in duplicate. For details of the collagen matrix implantation procedure, see, for example, U.S. Pat. No. 4,968,590, hereby incorporated by reference. After 12 days, the implants were removed and evaluated for new bone formation by histological observation as described in U.S. Pat. No. 4,968,590. In all cases, the immunoreactive fractions were osteogenically active.

2.2 Morphogen Detection in Serum

Morphogen may be detected in serum using morphogen-specific antibodies. The assay may be performed using any standard immunoassay, such as Western blot (immunoblot) and the like. Preferably, the assay is performed using an affinity column to which the morphogen-specific antibody is bound and through which the sample serum then is poured, to selectively extract the morphogen of interest. The morphogen then is eluted. A suitable elution buffer may be determined empirically by determining appropriate binding and elution conditions first with a control (e.g., purified, recombinantly-produced morphogen.) Fractions then are tested for the presence of the morphogen by standard immunoblot, and the results confirmed by N-terminal sequencing. Preferably, the affinity column is prepared using monoclonal antibodies. Morphogen concentrations in serum or other fluid samples then may be determined using standard protein quantification techniques, including by spectrophotometric absorbance or by quantitation of conjugated antibody.

Presented below is a sample protocol for identifying OP-1 in serum. Following this general methodology other morphogens may be detected in body fluids, including serum. The identification of morphogen in serum further indicates that systemic administration is a suitable means for providing therapeutic concentrations of a morphogen to an individual, and that morphogens likely behave systemically as endocrine-like factors. Finally, using this protocol, fluctuations in endogenous morphogen levels can be detected, and these altered levels may be used as an indicator of tissue dysfunction. Alternatively, fluctuations in morphogen levels may be assessed by monitoring morphogen transcription levels, either by standard northern blot analysis as described in Example 1, or by in situ hybridization, using a labelled probe capable of hybridizing specifically to morphogen RNA, and standard mRNA hybridization protocols well described in the art and described generally in Example 1.

OP-1 was detected in human serum using the following assay. A monoclonal antibody raised against mammalian, recombinantly produced OP-1 using standard immunology techniques well described in the art and described generally in Example 12, was immobilized by passing the antibody over an agarose-activated gel (e.g., Affi-Gel™, from Bio-Rad Laboratories, Richmond, CA, prepared following manufacturer's instructions) and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Fractions then were collected and tested for the presence of OP-1 by standard immunoblot using an OP-1 specific antibody as for Example 2.A.

Administered or endogenous morphogen levels may be monitored in the therapies described herein by comparing the quantity of morphogen present in a body fluid sample with a predetermined reference value, for example, to evaluate the efficiency of a therapeutic protocol, and the like. In addition, fluctuations in the level of endogenous morphogen antibodies may be detected by this method, most likely in serum, using an antibody or other binding protein capable of interacting specifically with the endogenous morphogen antibody. Detected fluctuations in the levels of the morphogen or endogenous antibody may be used, for example, as indicators of a change in tissue status. For example, as damaged tissue is regenerated and the tissue or organ's function returns to "normal" and, in the absence of additional tissue damage, lower doses of morphogen may be required, and a higher level of circulating morphogen antibody may be measured.

Example 3

Effect of Morphogen after the Onset of the Ischemic Process

The cardioprotective effect of morphogens following ischemic-reperfusion injury in a mammal can readily be assessed in a rat model. In this example, morphogen (e.g., OP-1) is administered just prior to the onset of the ischemic process in experimentally-induced myocardial infarcted rats, essentially following the method of Lefer, et al. (1990) *Science* 249:61–64 and (1992) *J. Mol. Cell. Cardiol.* 24: 385–393, the disclosures of which are hereby incorporated by reference. Briefly, loss of myocardial tissue function following ischemia and reperfusion is assayed by measuring loss of myocardial creatine kinase activity (CK) and loss of endothelium-dependent vasorelaxation function (see Example 4, below).

In a first group of ether-anesthetized rats, the left coronary artery was occluded just proximal to the first main branch with a silk ligature to induce a myocardial infarction (MI). The ligature was removed 10 minutes after occlusion to allow for coronary reperfusion. This first group is referred to herein as the "myocardial infarcted" (MI) group. A second group of rats underwent the same procedure-except that the coronary artery was not occluded, and thus no myocardial infarction occurred. The second group of rats is referred to herein as the "sham myocardial infarcted group" (SHAM MI).

The first group of rats, the MI group of rats, further was divided into three sub-groups. 2 µg of morphogen (OP-1) were injected intravenously into the first sub-group of MI rats 10 minutes after ligature, immediately before reperfusion; into the second sub-group of MI rats 20 µg of OP-1 were injected intravenously 10 minutes after ligature and immediately before reperfusion; and into the third sub-group of MI rats (control) was injected vehicle only, e.g., 0.9% NaCl, as for the OP-1 treated rats.

Twenty-four hours later, the hearts were removed from all of the rats and the levels of creatine kinase (CK) from the left ventricle (the infarcted region) and from the interventricular septum (the control nonischemic region) were determined by standard means. By comparing the difference in CK activities in both regions, the amount of CK activity lost from the infarcted region was used as an index of cardiac cellular injury to the infarcted region.

As shown in FIG. 1, the data indicate that morphogens (e.g., OP-1) can provide significant cardioprotective effect when provided to ischemic tissue. In the figure, CK loss is graphed as the difference in specific CK activity between the interventricular septum and the left ventricle.

The loss of CK activity by the subgroup of MI rats which received 2 μg of OP-1 just before reperfusion showed some protection as compared with the control MI rats which received injections of vehicle alone, when the levels from both subgroups are measured against, and compared to, the levels obtained for the SHAM MI control. Significant cardioprotection was observed in the subgroup of MI rats which received 20 μg of OP-1 immediately before reperfusion as compared with the control MI rats which received injections of vehicle alone, when the levels from both subgroups are measured against, and compared to, the levels contained within the SHAM MI control.

These data indicate that OP-1 offers significant cardiac protection when administered after ischemia and before reperfusion.

A variation of this example also may be performed providing morphogen to the animal prior to induction of ischemia. The experiments may be performed both in normal and immune-compromised rats to assess the cardioprotective effects of morphogen administered prior to ischemia.

Example 4

Vasodilation of Myocardial Infarcted Cardiac Tissue Treated with Morphogen

Certain vasodilators like acetylcholine (ACh) and adenosine diphosphate (ADP, an immune mediator) exert their vasodilation activity only in the presence of intact endothelium, which is stimulated to release a substance termed endothelium-derived relaxing factor (EDRF). If the endothelium is injured so that EDRF is not released, no vasodilation occurs in response to these endothelium-dependent agents. In contrast, several other vasodilators including nitroglycerine (NTG) and nitroprusside, are endothelium-independent dilators, as they dilate blood vessels directly.

The present example demonstrates the ability of OP-1 to prevent the loss of cardioendothelium-dependent relaxation (EDR) activity in the coronary microvasculature following reperfusion of ischemic myocardium, and their ability to reduce myocardial injury 24 hours after morphogen treatment. Briefly, 2 or 24 hours after morphogen treatment ischemia-reperfusion injury is induced in isolated rat hearts, the reperfused hearts are are vasodilated with either ACh or NTG. In the absence of morphogen treatment, injured tissue should inhibit ACh-induced vasodilation, but not NTG-induced vasodilation. Morphogen treatment in expected to enhance ACh-induced vasodilation in the reperfused hearts.

Accordingly, 48 adult male Sprague-Dawley rats (250–330 g) were divided into eight groups of 6 rats each. Twelve rats were subjected to sham myocardial infarcts (SHAM MI) as described in Example 3. The hearts of the remaining 36 rats were isolated as follows: one set of twelve rats was injected intravenously with OP-1 24 hours prior to isolation of the heart; another set of rats was injected intravenously with 20 μg of OP-1 2 hours prior to isolation of the heart; the final group of rats was injected with vehicle only (e.g., 0.9% NaCl.). The rats then were anesthetized with pentobarbital sodium (35 mg/kg, intraperitonial); their hearts were isolated and perfused by the Langendorff method at a constant flow (15 ml/min) with oxygenated Krebs-Henseleit solution (Aoki et al. (1988) J. Pharmacol. 95:35).

Each group of rats then were divided into two subgroups of six rats each. Twenty minutes before reperfusion, coronary vasodilator response was measured by inducing constriction with 0.05 μmol U-44619 (9,11-methanoepoxyprostaglandin $H_2$) followed by a vasodilating agent 3 minutes later: subgroup one—15 nmol ACh; subgroup 2—15 nmol NTG and the increase in coronary perfusion pressure (CPP) level measured as an indication of vasodilation. When CPP levels returned to normal, the hearts were subjected to ischemia by reducing coronary infusion to 15% of control flow for 30 minutes, then reestablishing normal flow, i.e., reperfusion, for an additional 20 minutes.

The vasodilator response then was remeasured by constriction and administration of vasodilating agent as described above.

Figure 2:
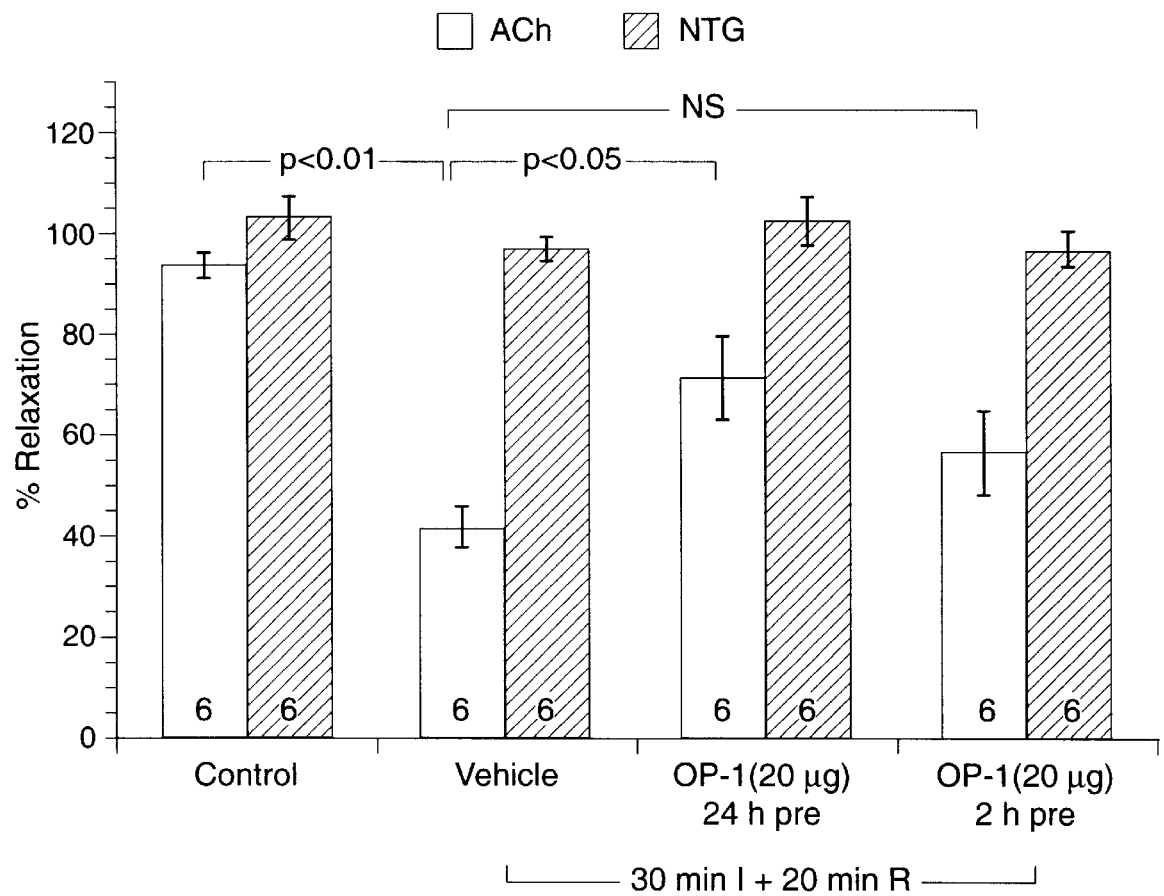
FIG. 2 shows the effects of 20 μg of morphogen (hOP1 given 24 hours prior to isolation of rat heart on endothelial-dependent vasorelaxation to acetycholine following induced ischemia-reperfusion injury.

The results of these experiments are shown in FIG. 2. Before the ischemic event, both Ach and NTG gave normal vasorelaxant results in all events. The hearts which received OP-1 24 hours prior to ischemia showed an approximately 70% response to ACh while the hearts which received OP-1 2 hours prior to ischemia showed a 55% response to ACh. The group which received vehicle alone showed a 40% response to ACh. Finally, the control group which was not subjected to ischemia showed an ACh response of approximately 95%. This shows that endothelium-dependent vasodilators exert a reduced vasodilator response following ischemia and reperfusion in the rat heart. Moreover, OP-1 significantly preserved endothelium-dependent dilation when provided 24 hours prior to induction of myocardial ischemia. No defect in vasodilation occurred in response to the direct vasodilator (NTG); NTG-induced vasodilation activities were 95% of initial in hearts subject to ischemia and 100% of initial nonischemic hearts.

Example 5

Effect of Morphogen on Neutrophil Adherence

The role of neutrophil adherence in endothelium dysfunction and the cardioprotective effects of morphogens in modulating this activity can be assessed using a standard polymorphonuclear neutrophil (PMN) adherence assay such as described in Lefer et al., (1992) J. Mol. Cell. Cardiol. 24: 385–393, disclosed hereinabove by reference. Briefly, segments of superior mesenteric artery were isolated from rats which had either been treated with morphogen (OP-1, 20 μg) or 0.9% NaCl, 24 h prior to isolation of the artery. The segments were cleaned, cut into transverse rings of 1–2 mm in length, and these were subsequently cut open and incubated in K—H solution at 37° C., pH 7.4. Neutrophils were prepared and fluorescently labelled using standard procedures (e.g., leukocytes were isolated from rats essentially following the procedure of Pertroft et. al. (1968) Exp Cell Res 50: 355–368, washed in phosphate buffered saline (PBS), purified by gradient centrifugation; and labelled by the method of Yuan et. al. (1990) Microvasc Res 40: 218–229.

Labelled neutrophils then were added to open ring baths and activated with 100 nM leukotriene $B_4$ ($LTB_4$). Rings were incubated for 20 minutes and the number of neutrophils adhering to the endothelial surface then determined visually by fluorescent microscopy.

Figure 3:
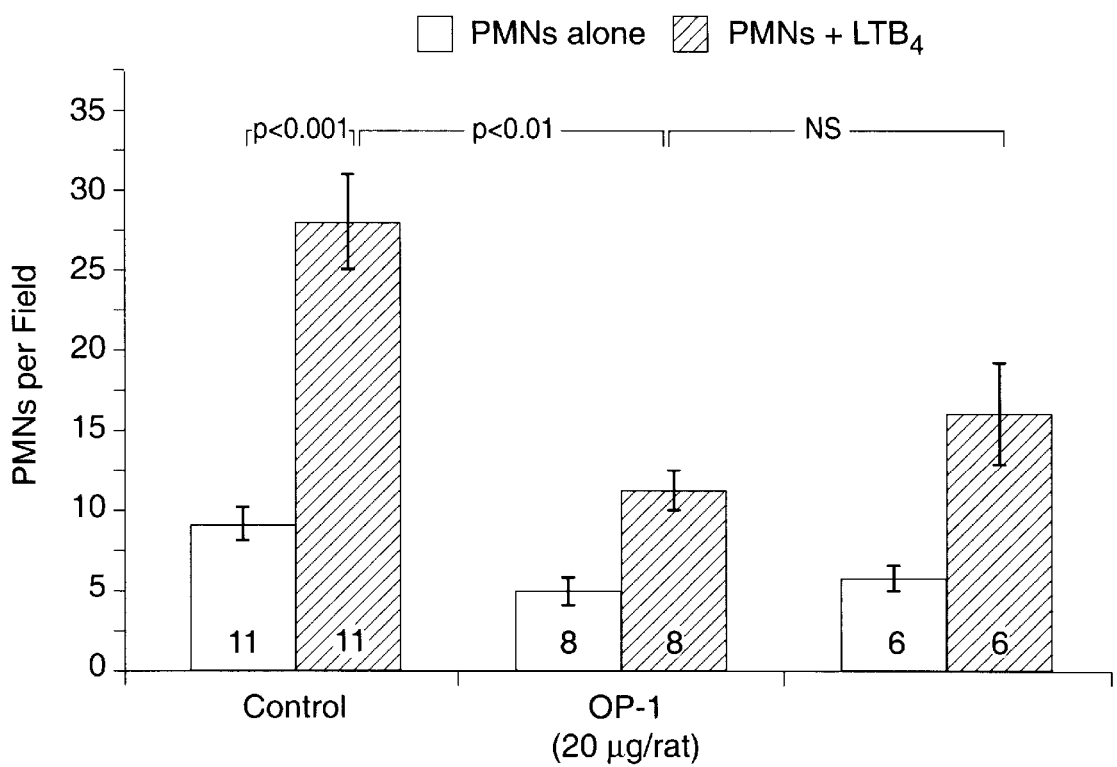
FIG. 3 shows the effect of morphogen (hOP1) on neutrophil adherence to $LTB_4$-stimulated mesenteric artery endothelium in neutrophil-activated rats.

As shown in FIG. 3, unstimulated PMNs (i.e., PMNs alone) added to the baths did not significantly adhere to the vascular endothelium. In rings taken from rats injected with 0.9% NaCl, activation of neutrophils with $LTB_4$ (100 nM) greatly increased the number of PMNs adherent to the endothelium (P<0.001). OP-1 (20 µg administered 24 h prior) significantly inhibited adherence of PMNs activated by $LTB_4$ (P<0.01 from control).

Example 6

Morphogen Inhibition of Cellular and Humoral Inflammatory Response

Figure 4B:
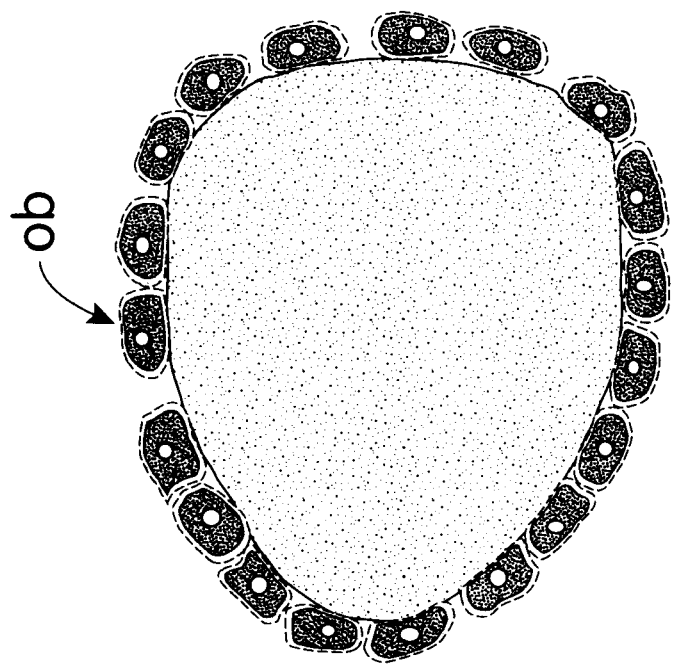
FIGS. 4(A and B) are schematic representations of morphogen inhibition of early mononuclear phagocytic multi-nuclearization in vivo.
Figure 4A:
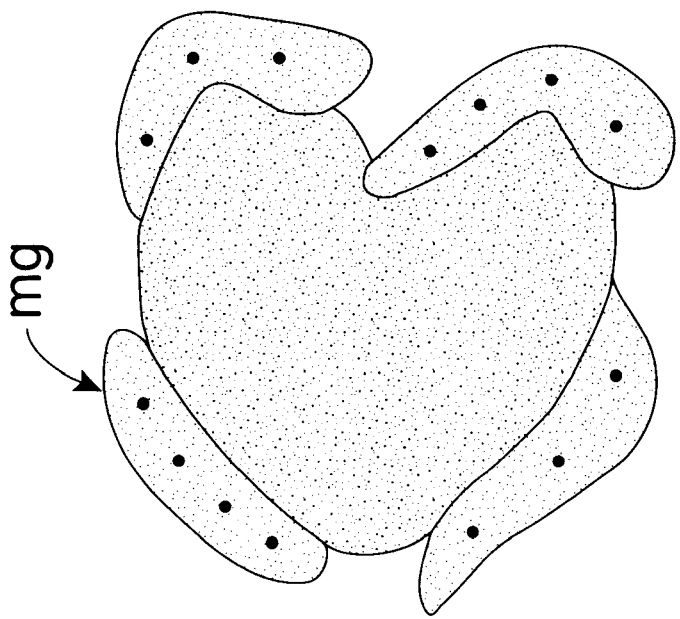
Figure 5A:
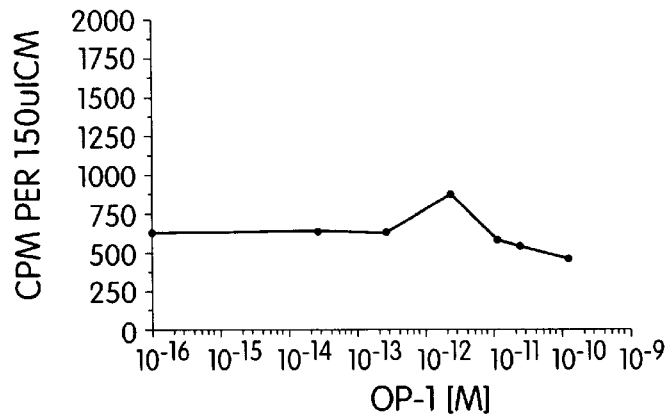
FIGS. 5(A–D) graphs the effects of a morphogen (eg., OP-1, FIGS. 5A and 5C) and TGF-β (FIG. 5B and 5D) on collagen (5A and 5B) and hyaluronic acid (5C and 5D) production in primary fibroblast cultures.
Figure 5B:
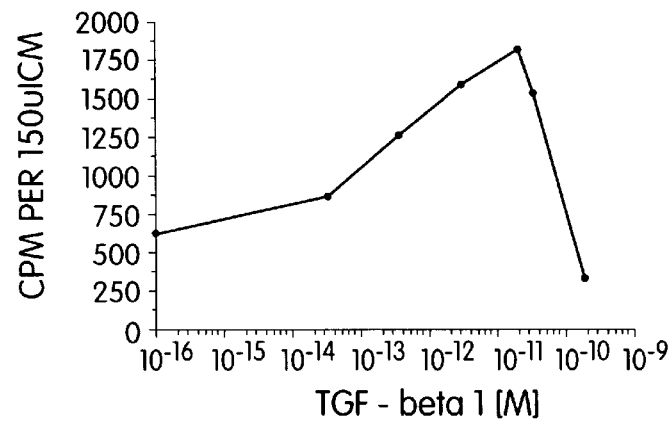
Figure 5C:
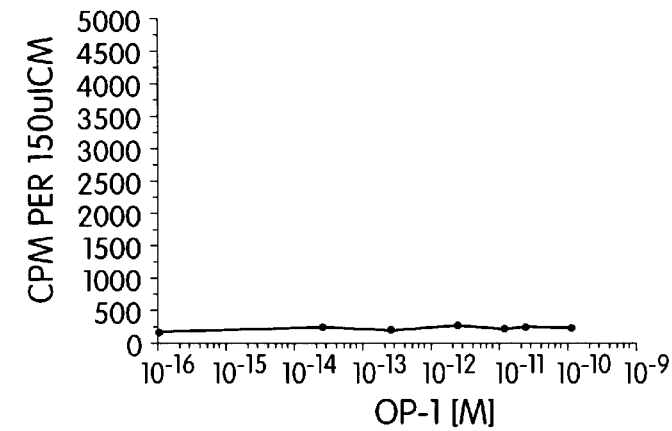
Figure 5D:
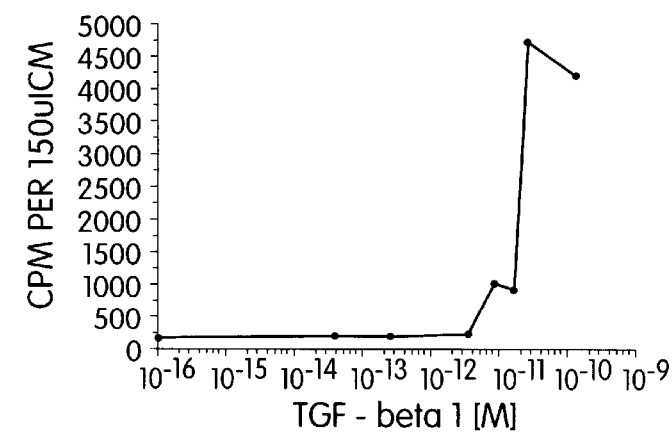

Morphogens described herein inhibit multinucleation of mononuclear phagocytic cells under conditions where these cells normally would be activated, e.g., in response to a tissue injury or the presence of a foreign substance. For example, in the absence of morphogen, an implanted substrate material (e.g., implanted subcutaneously) composed of, for example, mineralized bone, a ceramic such as titanium oxide or any other substrate that provokes multinucleated giant cell formation, rapidly becomes surrounded by multinucleated giant cells, e.g., activated phagocytes stimulated to respond and destroy the foreign object. In the presence of morphogen however, the recruited cells remain in their mononuclear precursor form and the matrix material is undisturbed. FIG. 4 illustrates this effect of morphogens, in a schematic representation of histology results of a titanium oxide substrate implanted subcutaneously. In the figure, "mg" means mononuclear giant cells and "ob" means osteoblasts. The substrate represented in FIG. 4B was implanted together with morphogen (OP-1) and newly formed osteoblasts are evident surrounding the substrate. By contrast, the substrate represented in FIG. 4A was implanted without morphogen and extensive multinucleated giant cell formation is evident surrounding the substrate. Accordingly, the morphogens' effect in inhibiting excessive bone mass loss in a mammal also may include inhibiting activation of these cells.

In addition, the morphogens described herein also suppress antibody production stimulated in response to a foreign antigen in a mammal. Specifically, when bovine bone collagen matrix alone was implanted in a bony site in a rat, a standard antibody response to the collagen is stimulated in the rat as determined by standard anti-bovine collagen ELISA experiments performed on blood samples taken at four week intervals following implantation (e.g., between 12 and 20 weeks.) Serum anti-collagen antibody titers, measured by ELISA essentially following the procedure described by Nagler-Anderson et al, (1986) *PNAS* 83:7443–7446, the disclosure of which is incorporated herein by reference, increased consistently throughout the experiment. However, when the matrix was implanted together with a morphogen (e.g., OP-1, dispersed in the matrix and adsorbed thereto, essentially as described in U.S. Pat. No. 4,968,590) anti-bovine collagen antibody production was suppressed significantly. This ability of morphogen to suppress the humoral response is further evidence of morphogen utility in alleviating tissue damage associated with autoimmune diseases, including autoantibody diseases, such as rheumatoid arthritis.

Example 7

Morphogen Effect on Fibrogenesis and Scar Tissue Formation

The morphogens described herein induce tissue morphogenesis of damaged or lost tissue. The ability of these proteins to regenerate new tissue enhances the anti-inflammatory effect of these proteins. Provided below are a series of in vitro experiments demonstrating the ability of morphogens to induce migration and accumulation of mesenchymal cells. In addition, the experiments demonstrate that morphogens, unlike TGF-β, do not stimulate fibrogenesis or scar tissue formation. Specifically, morphogens do not stimulate production of collagen, hyaluronic acid (HA) or metalloproteinases in primary fibroblasts, all of which are required for fibrogenesis or scar tissue formation. By contrast, TGF-β, a known inducer of fibrosis, but not of tissue morphogenesis, does stimulate production of these fibrosis markers.

Chemotaxis and migration of mesenchymal progenitor cells were measured in modified Boyden chambers essentially as described by Fava, R. A. et al (1991) *J. Exp. Med.* 173: 1121–1132, the disclosure of which is incorporated herein by reference, using polycarbonate filters of 2, 3 and 8 micron ports to measure migration of progenitor neutrophils, monocytes and fibroblasts. Chemotaxis was measured over a range of morphogen concentrations, e.g., $10^{-20}$M to $10^{-12}$M OP-1. For progenitor neutrophils and monocytes, $10^{-18}$–$10^{-17}$M OP-1 consistently induced maximal migration, and $10^{-14}$ to $10^{-13}$M OP-1 maximally induced migration of progenitor fibroblasts. In all cases the chemotactic activity could be inhibited with anti-OP-1 antibody. Similar migration activities also were measured and observed with TGF-β.

The effect of morphogen on fibrogenesis was determined by evaluating fibroblast production of hyaluronic acid (HA), collagen, collagenese and tissue inhibitor of metalloproteinases (TIMP).

Human fibroblasts were established from explants of infant foreskins and maintained in monolayer culture using standard culturing procedures. (See, for example, (1976) *J. Exp. Med.* 144: 1188–1203.) Briefly, fibroblasts were grown in maintenance medium consisting of Eagle's MEM, supplemented with nonessential amino acids, ascorbic acid (50 µg/ml), $NaHCO_3$ and HEPES buffers (pH 7.2), penicillin (100 U/ml), streptomycin (100 µg/ml), amphotericin B (1 µg/ml) and 9% heat inactivated FCS. Fibroblasts used as target cells to measure chemotaxis were maintained in 150 mm diameter glass petri dishes. Fibroblasts used in assays to measure synthesis of collagen, hyaluronic acid, collagenase and tissue inhibitors of metalloproteinases (TIMP) were grown in 100 mm diameter plastic tissue culture petri dishes.

The effects of morphogen on fibroblast production of hyaluronic acid, collagens, collagenase and TIMP were determined by standard assays (See, for example, Postethwaite et al. (1989) *J. Clin. Invest.* 83: 629–636, Postethwaithe (1988) *J./Cell Biol.* 106: 311–318 and Clark et al (1985) *Arch. Bio-chem Biophys.* 241: 36–44, the disclosures of which are incorporated by reference.) For these assays, fibroblasts were transferred to 24-well tissue culture plates at a density of 8×10⁴ cells per well. Fibroblasts were grown to confluency in maintenance medium containing 9% FCS for 72 h and then grown in serum-free maintenance medium for 24 h. Medium was then removed from each well and various concentrations of OP-1 (recombinantly produced mature or soluble form) or TGF-β-1 (R&D Systems, Minneapolis) in 50 µl PBS were added to triplicate wells containing the confluent fibroblast monolayers. For experiments that measured production of collagenase and TIMP, maintenance medium (450 µl) containing 5% FCS was added to each well, and culture supernatants were harvested from each well 48 h later and stored at −70° C. until assayed. For experiments that assessed HA production, maintenance medium (450 μl) containing 2.5% FCS was added to each well, and cultures grown for 48 h. For experiments that measured fibroblast production of collagens, serum-free maintenance medium (450 μl) without non-essential amino acids was added to each well and cultures grown for 72 h. Fibroblast production of HA was measured by labeling newly synthesized glycosaminoglycans (GAG) with [$^3$H]-acetate the last 24 h of culture and quantitating released radioactivity after incubation with hyaluronidase from *Streptomyces hyalurolyticus* (ICN Biochemicals, Cleveland, Ohio) which specifically degrades hyaluronic acid. Production of total collagen by fibroblasts was measured using a collagenase-sensitive protein assay that reflects [$^3$H]-proline incorporation the last 24 h of culture into newly synthesized collagens. Collagenase and TIMP protein levels in fibroblast cultures supernatants was measured by specific ELISAS.

As shown in FIG. 5, OP1 does not stimulate significant collagen or HA production, as compared with TGF-β. In the figure, panel A shows OP-1 effect on collagen production, panel B shows TGF-β effect on collagen production, and panels C and D show OP-1 (panel C) and TGF-β (panel D) effect on HA production. The morphogen results were the same whether the soluble or mature form of OP1 was used. By contrast, the latent form of TGF-β (e.g., pro domain-associated form of TGF-β) was not active.

Example 8

Screening Assay for Candidate Compounds which Alter Endogenous Morphogen Levels

Candidate compound(s) which may be administered to affect the level of a given morphogen may be found using the following screening assay, in which the level of morphogen production by a cell type which produces measurable levels of the morphogen is determined with and without incubating the cell in culture with the compound, in order to assess the effects of the compound on the cell. This can be accomplished by detection of the morphogen either at the protein or RNA level. A more detailed description also may be found in U.S. Ser. No. 752,861 commonly owned and now abandoned, currently pending as Ser. No. 08/278,729, incorporated hereinabove by reference.

8.1 Growth of Cells in Culture

Cell cultures of kidney, adrenals, urinary bladder, brain, or other organs, may be prepared as described widely in the literature. For example, kidneys may be explanted from neonatal or new born or young or adult rodents (mouse or rat) and used in organ culture as whole or sliced (1–4 mm) tissues. Primary tissue cultures and established cell lines, also derived from kidney, adrenals, urinary, bladder, brain, mammary, or other tissues may be established in multiwell plates (6 well or 24 well) according to conventional cell culture techniques, and are cultured in the absence or presence of serum for a period of time (1–7 days). Cells may be cultured, for example, in Dulbecco's Modified Eagle medium (Gibco, Long Island, N.Y.) containing serum (e.g., fetal calf serum at 1%–10%, Gibco) or in serum-deprived medium, as desired, or in defined medium (e.g., containing insulin, transferrin, glucose, albumin, or other growth factors).

Samples for testing the level of morphogen production includes culture supernatants or cell lysates, collected periodically and evaluated for OP-1 production by immunoblot analysis (Sambrook et al., eds., 1989, Molecular Cloning, Cold Spring Harbor Press, Cold Spring Harbor, N.Y.), or a portion of the cell culture itself, collected periodically and used to prepare polyA+ RNA for RNA analysis. To monitor de novo OP-1 synthesis, some cultures are labeled according to conventional procedures with an $^{35}$S-methionineI/$^{35}$S-cysteine mixture for 6–24 hours and then evaluated to determine OP-1 synthesis by conventional immunoprecipitation methods.

8.2 Determination of Level of Morphogenic Protein

In order to quantitate the production of a morphogenic protein by a cell type, an immunoassay may be performed to detect the morphogen using a polyclonal or monoclonal antibody specific for that protein. For example, OP-1 may be detected using a polyclonal antibody specific for OP-1 in an ELISA, as follows.

1 μg/100 μl of affinity-purified polyclonal rabbit IgG specific for OP-1 is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 μl aliquot of an appropriate dilution of each of the test samples of cell culture supernatant is added to each well in triplicate and incubated at 37° C. for 30 min. After incubation, 100 μl biotinylated rabbit anti-OP-1 serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala. diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3 M sulphuric acid. The OD at 490 nm of the solution in each well is recorded. To quantitate OP-1 in culture media, a OP-1 standard curve is performed in parallel with the test samples.

Polyclonal antibody may be prepared as follows. Each rabbit is given a primary immunization of 100 ug/500 μl E. *coli* produced OP-1 monomer (amino acids 328–431 in SEQ ID NO:5) in 0.1% SDS mixed with 500 μl Complete Freund's Adjuvant. The antigen is injected 30 subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against OP-1 is detected in the serum using an ELISA assay. Then, the rabbit is boosted monthly with 100 pg of antigen and bled (15 ml per bleed) at days seven and ten after boosting.

Monoclonal antibody specific for a given morphogen may be prepared as follows. A mouse is given two injections of *E. coli* produced OP-1 monomer. The first injection contains 100 μg of OP-1 in complete Freund's adjuvant and is given subcutaneously. The second injection contains 50 μg of OP-1 in incomplete adjuvant and is given intraperitoneally. The mouse then receives a total of 230 μg of OP-1 (amino acids 307–431 in SEQ ID NO:5) in four intraperitoneal injections at various times over an eight month period. One week prior to fusion, both mice are boosted intraperitoneally with 100 μg of OP-1 (307–431) and 30 μg of the N-terminal peptide (Ser$_{293}$-Asn$_{309}$-Cys) conjugated through the added cysteine to bovine serum albumin with SMCC crosslinking agent. This boost was repeated five days (IP), four days (IP), three days (IP) and one day (IV) prior to fusion. The mouse spleen cells are then fused to myeloma (e.g., 653) cells at a ratio of 1:1 using PEG 1500 (Boeringer Mannheim), and the cell fusion is plated and screened for OP-1-specific antibodies using OP-1 (307–431) as antigen. The cell fusion and monoclonal screening then are according to standard procedures well described in standard texts widely available in the art.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for preserving ex vivo viability of an organ or tissue for transplantation, the method comprising:
   contacting said organ or tissue with a morphogen other than TGF-$\beta_2$, said morphogen comprising a dimeric protein having an amino acid sequence selected from the group consisting of
   (i) a sequence having at least 70% amino acid sequence homology with the C-terminal seven-cysteine skeleton of human OP-1, amino acids 38–139 of Seq. ID No. 5; and
   (ii) Generic Sequence 6, Seq. ID No. 31;
   wherein said morphogen induces endochondral bone formation in an in vivo assay.

2. A method for removing an organ or tissue from a donor host for transplantation to a recipient host, said method comprising the steps of:
   (a) contacting said organ or tissue with a morphogen other than TGF-$\beta_2$, said morphogen comprising a dimeric protein having an amino acid sequence selected from the group consisting of
      (i) a sequence having at least 70% amino acid sequence homology with the C-terminal seven-cysteine skeleton of human OP-1, amino acids 38–139 of Seq. ID No. 5; and
      (ii) Generic Sequence 6, Seq. ID No. 31;
      wherein said morphogen induces endochondral bone formation in an in vivo assay; and
   (b) removing said organ or tissue from said donor host.

3. A method for implanting a donor organ or tissue in a recipient host, the method comprising:
   (a) contacting said donor organ or tissue with a morphogen other than TGF-$\beta_2$, said morphogen comprising a dimeric protein having an amino acid sequence selected from the group consisting of
      (i) a sequence having at least 70% amino acid sequence homology with the C-terminal seven-cysteine skeleton of human OP-1, amino acids 38–139 of Seq. ID No. 5; and
      (ii) Generic Sequence 6, Seq. ID No. 31;
      wherein said morphogen induces endochondral bone formation in an in vivo assay; and
   (b) implanting said organ or tissue in said recipient host.

4. A method for transporting an organ or tissue removed from a donor host for implantation into a recipient host, the method comprising:
   (a) placing said organ or tissue in a preservation solution comprising a morphogen other than TGF-$\beta_2$, said morphogen being dispersed in a fluid formulation having an osmotic pressure substantially equivalent to the osmotic pressure of living mammalian cells,
      said morphogen comprising a dimeric protein having an amino acid sequence selected from the group consisting of
      (i) a sequence having at least 70% amino acid sequence homology with the C-terminal seven-cysteine skeleton of human OP-1, amino acids 38–139 of Seq. ID No. 5; and
      (ii) Generic Sequence 6, Seq. ID No. 31;
      wherein said morphogen induces endochondral bone formation in an in vivo assay; and
   (b) transporting said organ or tissue to the recipient host.

5. The method of claim 1, 2, 3, or 4 wherein said organ is selected from the group consisting of lung, heart, kidney, liver, and pancreas.

6. The method of claim 1, 2, 3, or 4 wherein said tissue is selected from the group consisting of skin, bone marrow, and gastrointestinal mucosa tissue.

* * * * *